(12) United States Patent
Spohn et al.

(10) Patent No.: US 9,314,565 B2
(45) Date of Patent: *Apr. 19, 2016

(54) INJECTOR SYSTEM FOR ENCODING AND SENSING OF SYRINGE INFORMATION

(71) Applicant: Bayer Healthcare LLC, Indianola, PA (US)

(72) Inventors: Michael A. Spohn, Butler, PA (US); Joelle A. Rudnick, Moon Township, PA (US); Thomas P. Joyce, Wilkins Township, PA (US); Adam J. Hahn, Pittsburgh, PA (US); Michael J. Masters, Jeannette, PA (US); William J. Nolan, Curtisville, PA (US); Jason A. Zaperach, Springdale, PA (US); Joseph B. Havrilla, Pittsburgh, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 73 days.

This patent is subject to a terminal disclaimer.

(21) Appl. No.: 13/845,053

(22) Filed: Mar. 17, 2013

(65) Prior Publication Data
US 2013/0226090 A1 Aug. 29, 2013

Related U.S. Application Data

(62) Division of application No. 12/419,019, filed on Apr. 6, 2009, now Pat. No. 8,439,876, which is a division of application No. 10/114,710, filed on Apr. 2, 2002, now abandoned.

(60) Provisional application No. 60/281,169, filed on Apr. 30, 2001.

(51) Int. Cl.
*A61M 5/00* (2006.01)
*A61M 5/142* (2006.01)
*A61M 5/145* (2006.01)

(52) U.S. Cl.
CPC ............... *A61M 5/142* (2013.01); *A61M 5/007* (2013.01); *A61M 5/14566* (2013.01);
(Continued)

(58) Field of Classification Search
CPC ............ A61M 2205/6063; A61M 2205/6018; A61M 5/007; A61M 5/14566; A61M 5/142
USPC ................. 604/131, 151, 152, 154, 155, 189; 600/432
See application file for complete search history.

(56) References Cited

U.S. PATENT DOCUMENTS

| 4,006,736 A | 2/1977 | Kranys et al. |
| 4,278,086 A | 7/1981 | Hodgins et al. |

(Continued)

FOREIGN PATENT DOCUMENTS

| WO | 97/36635 | 10/1997 |
| WO | 98/00187 | 1/1998 |

(Continued)

*Primary Examiner* — Matthew F Desanto
(74) *Attorney, Agent, or Firm* — David Schramm; Joseph L. Kent; James R. Stevenson

(57) ABSTRACT

Injector systems which include a syringe and a powered injector to inject a fluid into a patient are described. The powered injector includes a drive member, an energy source, at least one sensor for detecting energy from the energy source, and at least one contact member axially movable in the injector and in communication with the sensor. The syringe includes at least one indicator positioned at a predetermined position, such as on a rear surface of an attachment flange, which may transmit or reflect energy from the energy source to the sensor. The contact member may contact and be moved by the indicator when the syringe is attached to the powered injector, so that the energy detected by the sensor may be determined by the position of the indicator. The position of the indicator thereby provides information about the syringe configuration.

14 Claims, 17 Drawing Sheets

(52) U.S. Cl.
CPC ... *A61M 5/14546* (2013.01); *A61M 2205/6018* (2013.01); *A61M 2205/6036* (2013.01); *A61M 2205/6063* (2013.01)

(56) References Cited

U.S. PATENT DOCUMENTS

| | | | |
|---|---|---|---|
| 4,650,475 A | 3/1987 | Smith et al. | |
| 4,978,335 A | 12/1990 | Arthur, III | |
| 5,383,858 A | 1/1995 | Reilly et al. | |
| 5,461,239 A * | 10/1995 | Atherton | 250/566 |
| 5,520,653 A | 5/1996 | Reilly et al. | |
| 5,531,698 A | 7/1996 | Olsen | |
| 5,535,746 A | 7/1996 | Hoover et al. | |
| 5,662,612 A | 9/1997 | Nieboff | |
| 5,741,232 A | 4/1998 | Reilly et al. | |
| 5,814,015 A * | 9/1998 | Gargano et al. | 604/67 |
| 5,873,861 A * | 2/1999 | Hitchins et al. | 604/218 |
| 5,928,197 A | 7/1999 | Niehoff | |
| 5,944,694 A | 8/1999 | Hitchins et al. | |
| 5,954,700 A | 9/1999 | Kovelman | |
| 5,997,502 A * | 12/1999 | Reilly et al. | 604/67 |
| 6,017,330 A | 1/2000 | Hitchins et al. | |
| 6,019,745 A * | 2/2000 | Gray | 604/131 |
| 6,090,064 A | 7/2000 | Reilly et al. | |
| 6,533,183 B2 * | 3/2003 | Aasmul et al. | 235/494 |
| 6,958,053 B1 | 10/2005 | Reilly | |
| 7,018,363 B2 | 3/2006 | Cowan et al. | |
| 7,462,166 B2 | 12/2008 | Cowan et al. | |
| 8,439,876 B2 * | 5/2013 | Spohn et al. | 604/131 |
| 8,821,450 B2 * | 9/2014 | Cowan et al. | 604/181 |
| 2001/0034506 A1 | 10/2001 | Hirschman et al. | |
| 2002/0000471 A1 | 1/2002 | Aasmul et al. | |
| 2002/0128606 A1 | 9/2002 | Cowan et al. | |
| 2003/0060754 A1 | 3/2003 | Reilly et al. | |

FOREIGN PATENT DOCUMENTS

| | | |
|---|---|---|
| WO | 99/65548 | 12/1999 |
| WO | 01/08727 | 2/2001 |
| WO | 01/37903 | 5/2001 |
| WO | 02/056934 | 7/2002 |

* cited by examiner

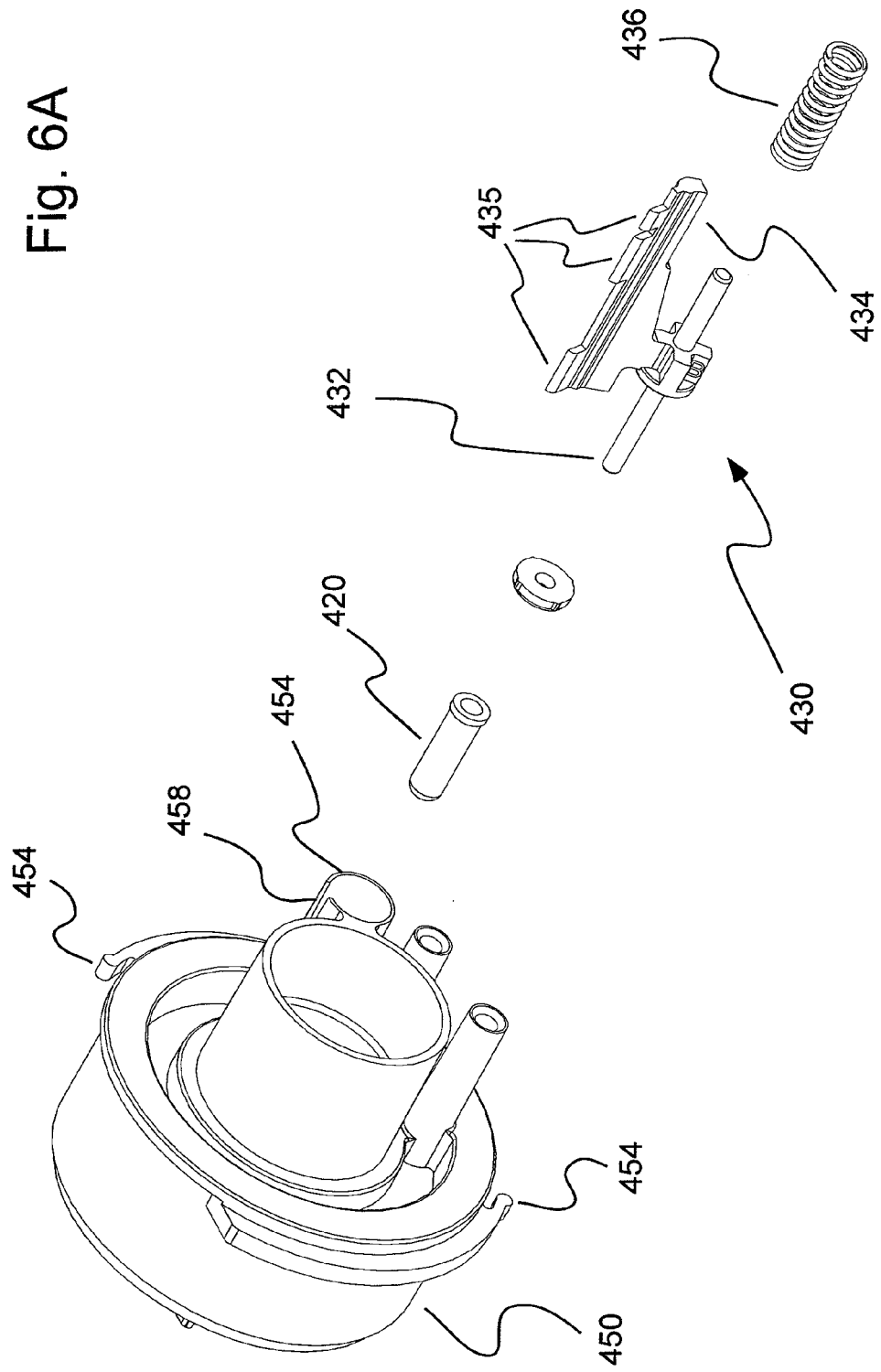

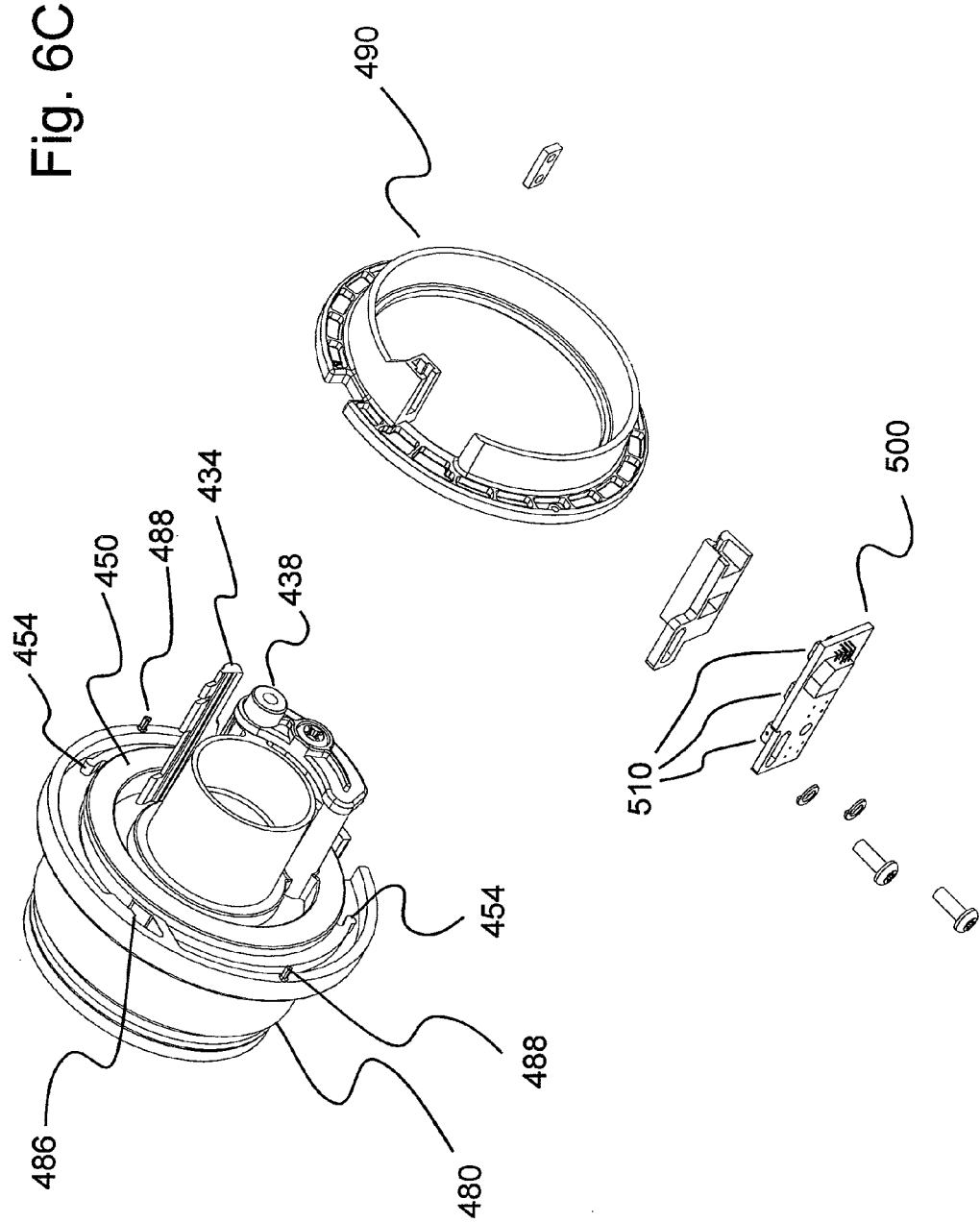

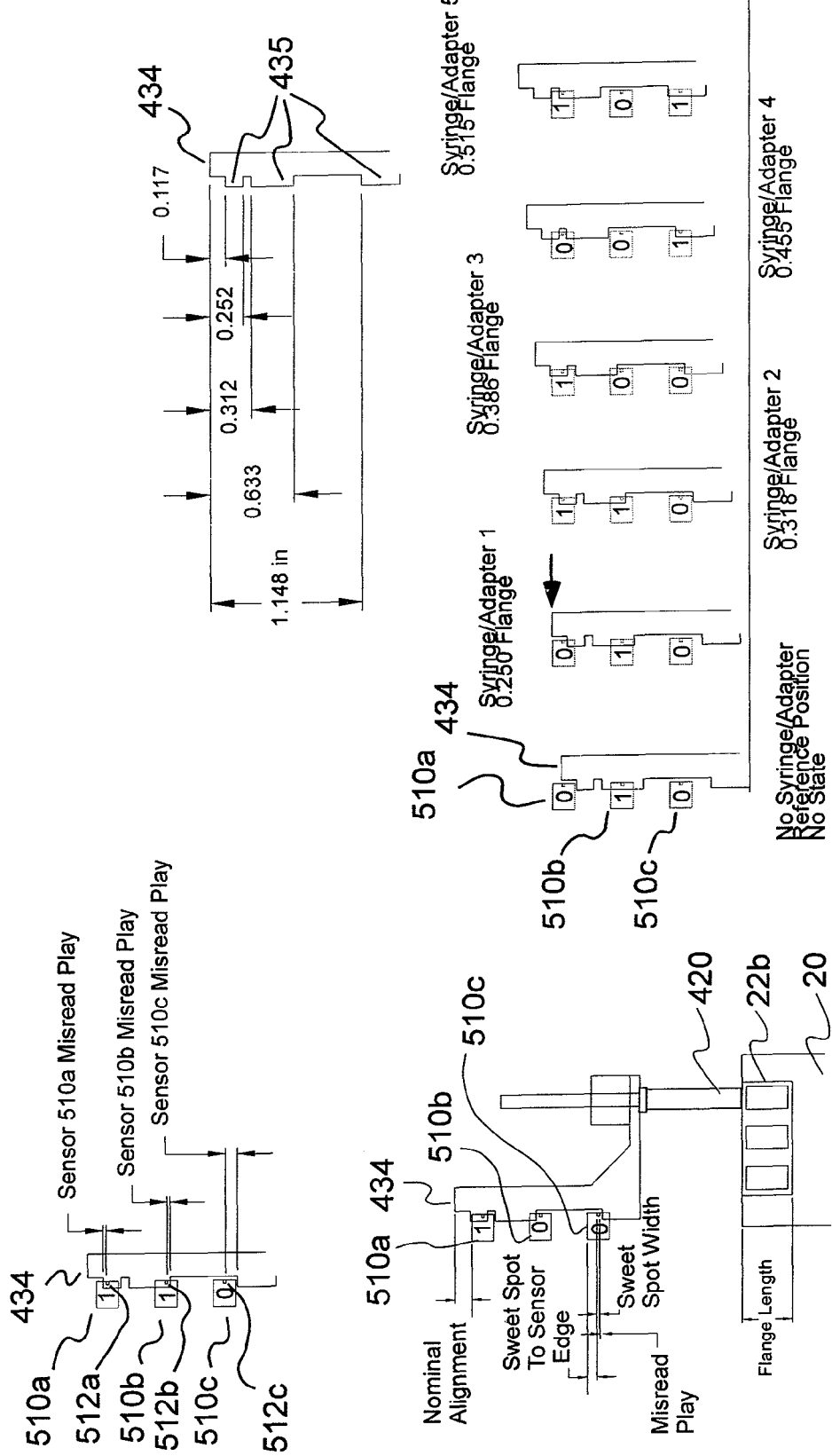

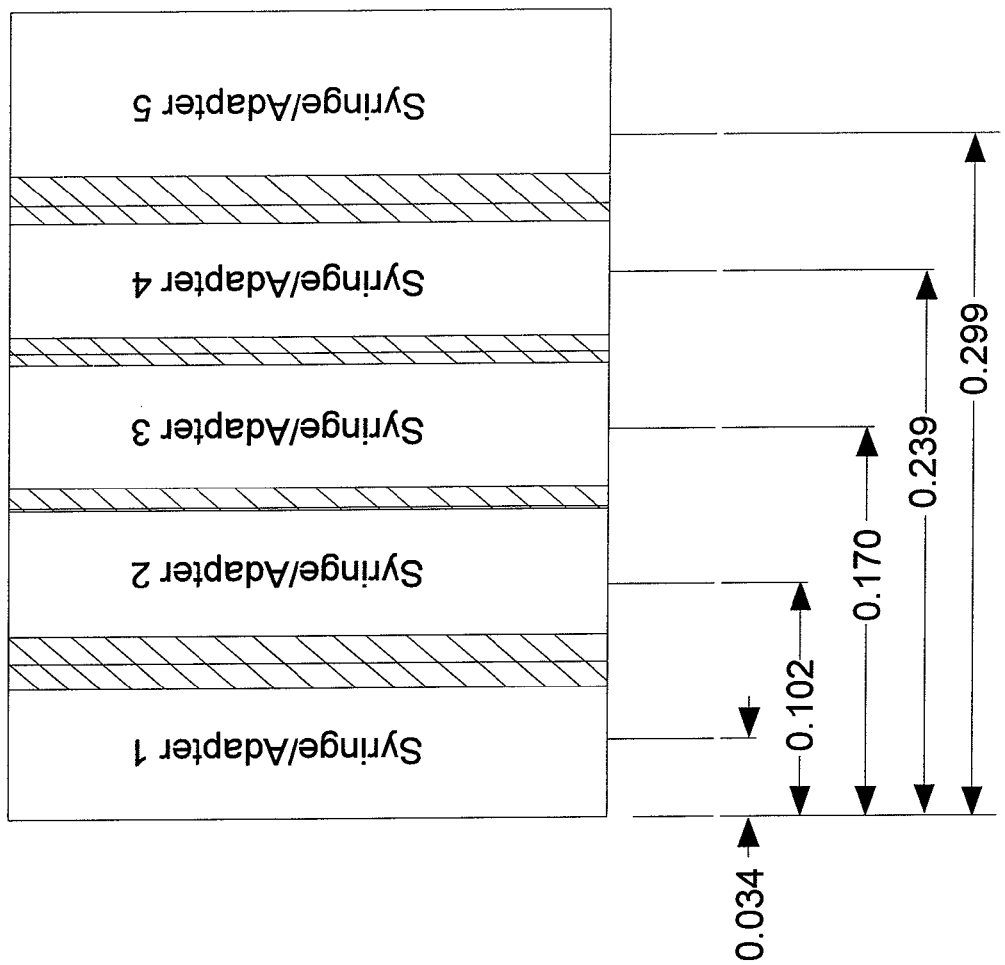

INJECTOR SYSTEM FOR ENCODING AND SENSING OF SYRINGE INFORMATION

CROSS-REFERENCE TO RELATED APPLICATION

This application is a divisional application of pending U.S. patent application Ser. No. 12/419,019, filed Apr. 6, 2009, now U.S. Pat. No. 8,439,876, issued May 14, 2013, which is a divisional application of U.S. patent application Ser. No. 10/114,710, filed on Apr. 2, 2002, now abandoned, which claims the benefit of U.S. Provisional Patent Appln. No. 60/281,169, filed on Apr. 3, 2001, the disclosures of which are each incorporated herein by reference as of set forth in their entirety.

BACKGROUND OF THE INVENTION

The present invention relates to encoding and sensing of information or configuration, and, especially, to encoded syringes, to injectors for reading encoded syringes, to injector systems including encoded syringes and to methods of encoding and sensing syringe information.

Critical parameters of an injection procedure are determined by a number of variables, including, for example, syringe diameter, syringe length, syringe material and fluid composition/concentration. Among the affected injection procedure parameters are fluid volume delivered, flow rate, fluid pressure, and limits of injector piston travel. In current injector systems, syringe size/volume is generally determined either (1) manually by action of an operator who enters the syringe size/volume or type into the injector software, or (2) automatically by means of switches on the injector head which are mechanically coupled to raised or sunken elements on the syringe. See, for example, U.S. Pat. Nos. 5,741,232, 6,090,064 and 5,873,861, assigned to the assignee of the present application, the disclosures of which are incorporated herein by reference. In U.S. Pat. No. 5,873,861, the presence or absence of one or more of detents provides a code that is representative of syringe configuration.

Constraints of current mechanical and electrical design, however, limit the number of such automatic detection switches. Indeed, only limited syringe configurations are automatically detected with present systems. Additionally, failure of certain moving mechanisms is also a problem. For example, spillage or leakage of contrast media can result in the failure of certain mechanisms. Moreover, certain electrical and mechanical encoding systems can significantly increase manufacturing costs of a syringe and/or injector. Other currently available methods of encoding and sensing syringe configuration include the placement of bar codes and corresponding sensors upon the syringe and injector, respectively, as disclosed in U.S. Pat. No. 5,997,502. Bar code systems, however, suffer from some of the same problems as the electromechanical systems discussed above.

As used herein, the term "syringe configuration" is used to encompass all information about a particular syringe, including, but not limited to, information about the mechanical properties of a syringe (for example, material, length, diameter and/or volume) as well as information about the contents of the syringe (for example, fluid volume and/or composition). With the advent of new syringes, and especially pre-filled syringes, the need to accurately encode and sense (or read) syringe configuration variables is heightened. A powered injector to control the injection procedure as a function of defined syringe configuration/injection parameters can use the information on syringe configuration. Moreover, a record of data associated with an injection procedure may be kept, for example, to track patient treatment history and/or to satisfy accurate billing and cost information requirements under managed health care. A record may be maintained of information such as the type of syringe used, the amount of contrast medium used, the type of contrast medium used, the sterilization date, the expiration date, lot codes, the properties of the contrast media, and/or other clinically relevant information. Such information can be recorded digitally for sharing with computerized hospital billing systems, inventory systems, control systems, etc.

SUMMARY OF THE INVENTION

In one aspect, the present invention provides a syringe for use with a powered injector to inject a fluid into a patient. The syringe includes at least a first indicator positioned on the syringe at a predetermined position (for example, at a predetermined axial position). Preferably, the distance between a surface (for example, a rear surface) of the first indicator and a reference position (for example, a predetermined position on the syringe or on the powered injector when the syringe is in operative connection with the powered injector) provides information about the syringe configuration.

In another aspect, the present invention provides a syringe including at least one indicator including a rearward-projecting member (for example, an attachment flange) on a rear portion of the syringe. The axial position of a rear surface of the rearward-projecting member, when the syringe is in operative connection with (for example, attached to) the powered injector, provides information about the syringe configuration.

In a further aspect, the present invention provides a set of a plurality of syringes for use with a powered injector to inject a fluid into a patient. Each of the syringes includes at least a first indicator positioned on the syringe at a predetermined position. As described above, the distance between, for example, a rear surface of the first indicator and a reference position such as a predetermined position on the powered injector provides information about a configuration of each syringe. In one embodiment, the first indicator on each syringe is a rear surface of an attachment flange positioned on a rearward portion of the syringe. The axial position of the rear surface of the attachment flange of each syringe in this embodiment provides information about the syringe configuration of that syringe when the syringe is in operative connection with the powered injector.

In general, the indicators of the present invention can be an integral part of a syringe or can be attachable thereto. For example, one or more indicators can be attachable to a syringe through use of an adapter as known in the art. A number of such adapters include a syringe attachment mechanism on a forward section thereof for attachment of a syringe thereto. The adapter also includes an injector attachment mechanism on a rearward section thereof to attach the adapter to an injector. An adapter can be used, for example, to attach a syringe not suitable for direct attachment to an injector to that injector. Adapters can also be used in the present invention to add an indicator as described above to a syringe that is otherwise suitable for attachment to an injector. For example, the adapter can include one or more attachment flanges having a rear surface positioned to provide information on syringe configuration. In general, as use herein, the term "syringe" includes syringe/adapter combinations.

In another aspect, the present invention provides an injector system including a powered injector having a drive member and at least one sensor for detecting energy. The injector system also includes a syringe having at least a first indicator positioned on the syringe at a predetermined position (for example, a predetermined axial position). The sensor configuration detected by the sensor is determined by the position of the indicator when the syringe is in operative connection with the powered injector. The position of the indicator thus provides information about the syringe configuration.

In one embodiment, a rear surface of the first indicator transmits energy to the sensor. For example, the rear surface of the first indicator can include an energy source to transmit energy to the sensor. The rear surface of the first indicator can also include a surface that transmits energy to the sensor by reflecting energy from an energy source to the sensor.

In another embodiment, the powered injector includes at least one contact member movably (for example, slidably) disposed in the injector. A surface in operative connection with the contact member transmits energy to the sensor. For example, the transmitting surface can be the rear surface of the contact member. The contact member is positioned to come into contact with the first indicator when the syringe is in operative connection with the powered injector such that, for example, the axial position of the rear surface of the contact member is determined by the axial position of the first indicator. The rear surface of the contact member can, for example, transmit energy to the sensor. For example, the rear surface of the contact member can include an energy source to transmit energy to the sensor. In another embodiment, the rear surface of the contact member includes a surface to reflect or redirect energy from an energy source to the sensor.

In several embodiments, the energy transmitted in the present invention is light energy. Reflective surfaces (for example, a mirrored surface) can be used on the contact member or on the indicator to transmit the light energy therefrom. The light can, for example, be transmitted to the mirrored surface by a transmitting fiber optic cable in communication with a light source. The mirrored surface can transmit the light to a receiving fiber optic cable in communication with a sensor. Sensors suitable for use with light energy include photodiodes.

In several embodiments, the first indicator is a rear surface of a flange or projection on a rear portion of the syringe. The flange can, for example, also function as an attachment flange to attach the syringe to a powered injector.

In another aspect, the present invention provides a powered injector for use with a syringe to inject a fluid into a patient. The syringe includes at least a first indicator at a predetermined position. The injector includes a powered drive member and at least one sensor to detect energy. The energy detected by the sensor is determined by the position of the indicator when the syringe is in operative connection with the powered injector. As discussed above, the position of the indicator thereby provides information about the syringe configuration.

As also described above, the injector can, for example, include a contact member movably (for example, slidably) disposed in the injector in which the rear surface of the contact member transmits energy to the sensor. The contact member is positioned to come into contact with the first indicator when the syringe is attached to the powered injector such that the position of the contact member is determined by the position of the first indicator.

In a further aspect, the present invention provides an injection system including at least one syringe having at least a first indicator positioned on the syringe at a predetermined position (for example, a rear surface of an attachment flange on the rear of the syringe). As described above, the position of the indicator is associated with information about the syringe configuration. The injector system further includes a powered injector including a drive member and at least a first contact member movably disposed in the injector. The first contact member is positioned to come into contact with the first indicator when the syringe is attached to the powered injector such that the position of the first contact member or the amount of change in the position of the first contact member is determined by the position of the first indicator and is thus associated with the syringe configuration.

Preferably, at least three syringe configurations are associated with at least three corresponding positions of the first contact member. As clear to one skilled in the art, many more syringe configuration are associable with a corresponding number of positions of the first contact member. Each syringe configuration can, for example, be associated with a unique range of positions of the first contact member.

In one embodiment, the powered injector includes at least one light reflective surface in operative connection with the first contact member and a sensor to detect light reflected from the light reflective surface as described above.

In another embodiment, the powered injector includes a plurality of sensors and at least a first shutter mechanism in operative connection with the first contact member. Each of the sensors has an "on" state and an "off" state. The shutter mechanism includes at least one cooperating member to cooperate with at least one of the sensors to place the sensor in an on state or an off state. The state of each of the plurality of sensors can, for example, provide a digital code corresponding to information on syringe configuration.

Preferably, the shutter mechanism includes a plurality of cooperating members. In one embodiment, the sensors are optical sensors and the cooperating members are spaced opaque members operable to block transmission of light to the sensors.

The present invention provides, in a further aspect, an injector for use with a syringe including at least a first indicator positioned thereon. The position of the first indicator is associated with syringe configuration. The injector includes a powered drive member, and at least a first contact member movably disposed in the injector as described above.

In one embodiment, the first indicator is positioned on the rear surface of an attachment flange of the syringe and causes the first contact member to move in an axial direction. The first contact member can, for example, be slidably positioned on a bushing that is rotatable about the axis of the syringe. In this embodiment, the shutter mechanism can be attached to the first contact member and is preferably rotated into cooperation with the plurality of sensors upon rotation of the bushing to attach the syringe to the injector.

In another aspect, the present invention provides a method of reading syringe configuration information from a syringe for use with a powered injector. The method includes (1) positioning at least a first indicator at a predetermined position on the syringe, (2) transmitting energy from a position determined by the indicator to a sensor on the powered injector, and (3) measuring an output from the sensor and correlating the output to a state distance defined by a distance between the first indicator and a known position on the injector. The state distance provides information of the syringe configuration.

In still a further aspect, the present invention provides a method of reading syringe configuration information from a syringe for use with a powered injector. The method includes (1) positioning at least a first indicator at a predetermined position on the syringe, (2) contacting the indicator with at least a first contact member movably disposed in the injector so that the position of the first contact member is determined by the position of the first indicator, and (3) associating the position of the contact member with syringe configuration. Preferably, at least three different syringe configurations are associated with at least three corresponding positions of the first contact member.

In one embodiment, the method includes the step of transmitting light energy from a surface in operative connection with the first contact member to a sensor. The light energy measured by the sensor corresponds to the position of the first contact member.

In another embodiment, a shutter mechanism in operative connection with the first contact member moves with motion of the contact member to a position that determines a state of each of a plurality of sensors having an on state and an off state. The state of each of the plurality of sensors provides or corresponds to a digital code corresponding to information on syringe configuration.

The encoded syringes, the injectors, the injectors systems, and the methods of the present invention are well suited for use in a magnetic resonance environment in which care must be taken to prevent failure of the encoding system or device and to prevent interference with the magnetic resonance imaging equipment. In that regard, the strong magnetic field in a magnetic resonance environment can adversely affect certain types of devices such as electromechanically activated devices. Furthermore, differences in magnetic permeability of materials within such devices and induced eddy currents therein can affect the homogeneity of the MRI magnetic field, generating image artifacts. Likewise, radio frequency energy generated by certain devices can induce unwanted artifacts upon the acquired MRI images. Such problems are easily avoided in the syringe encoding systems, devices and methods of the present invention. Any energy used in the encoding systems, devices and methods of the present invention is easily selected to prevent interference with magnetic resonance equipment as well as interference from the magnetic resonance equipment. For example, light energy in the infrared, visible or ultraviolet range of the spectrum can be used. Likewise, radio frequency energy outside of the frequency range of the MRI scanner can be used.

Moreover, currently available syringes and injectors are readily retrofitted to incorporate the encoding systems of the present invention without substantial and/or expensive modifications thereto.

BRIEF DESCRIPTION OF THE DRAWINGS

FIG. 6A illustrates a rear perspective view of an embodiment of a syringe interface of the present invention in a disassembled or exploded state.

FIG. 6C illustrates another rear perspective view of the syringe interface of FIG. 6A in another partially assembled state.

FIG. 8A illustrates dimensions of one embodiment of a shutter of the present invention as well as several states corresponding to different shutter positions resulting from engagement of various syringe/adapter types.

FIG. 8B illustrates engagement of the push pin or contact pin of the syringe interface of FIG. 6A by a syringe/adapter and tolerance analysis measurements associated with one embodiment of a shutter.

FIG. 8C illustrates state changes associated with the shutter and sensor embodiments of FIGS. 8A and 8B.

DETAILED DESCRIPTION OF THE INVENTION

The encoding devices, encoding systems and encoding methods of the present invention are particularly useful in encoding information of configuration for syringes and other pumping mechanisms used in medical injection procedures. Several representative embodiments of the present invention in which, for example, light energy is used in connection with syringe encoding are discussed below.

Figure 1:
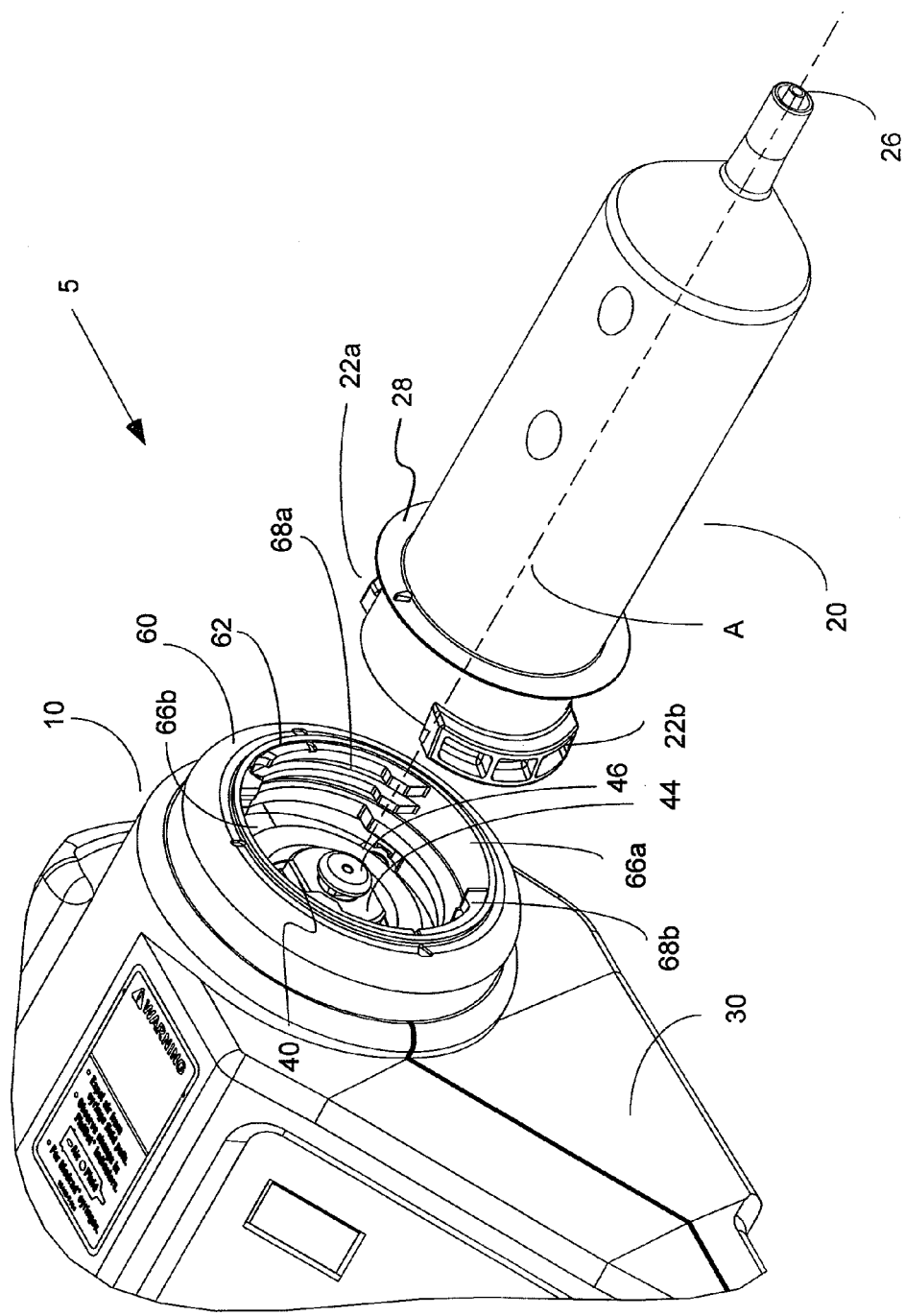
FIG. 1 illustrates a front perspective view of one embodiment of an injector system of the present invention.

An embodiment of a front-loading injector system 5 of the present invention is illustrated in FIG. 1. Injector system 5 includes a powered injector 10 and a syringe 20 for injection of, for example, a contrast medium. As best illustrated in FIG. 1, injector housing 30 of injector 10 preferably includes a first drive member or piston 40 therein which cooperates with a syringe plunger 25 (see FIG. 2A) slideably disposed in syringe 20 to inject a fluid from the interior of syringe 20 into a patient.

As used herein to describe injection system 5 and other embodiments of the present invention, the terms "axial" or "axially" refer generally to, for example, an axis A around which syringe 20 and piston 40 are preferably formed (although not necessarily symmetrically therearound) and to directions collinear with or parallel to axis A. The terms "proximal" or "rearward" refer generally to an axial or a longitudinal direction toward the end of injector housing 30 opposite the end to which syringe 20 is mounted. The terms "distal" or "forward" refer generally to an axial or a longitudinal direction toward a syringe tip 26 of syringe 20 (from which pressurized fluid exits syringe 20). The term "radial" refers generally to a direction normal to an axis such as axis A.

Syringe 20 is preferably removably connected to injector 10 as described, for example, in U.S. Pat. No. 5,383,858, the disclosure of which is incorporated herein by reference. In that regard, front-loading injector 10 can include a front portion or faceplate 60 having a first interface 62 formed therein. Piston 40 is reciprocally mounted within injector 10 and is extendible through interface 62 in faceplate 60. Piston 40 can, for example, include a piston flange or head 44 to assist in forming a connection with syringe plunger 25. In the embodiment of FIG. 1, faceplate 60 includes receiving slots 66a and 66b, which are positioned opposite one another around interface 62. Receiving flanges 68a and 68b are positioned opposite one another and between receiving slots 66a and 66b and extend inwardly into interface 62.

In the embodiment of FIG. 1, the rearward end of syringe 20 includes a releasable mounting mechanism such as a pair of mounting flanges 22a and 22b for mounting syringe 20 in a desired position relative to the front wall of injector 10. To attach syringe 20 to injector 10, the rearward end of syringe 20 is inserted into injector interface 62 such that mounting flanges 22a and 22b are inserted into receiving slots 66a and 66b, respectively. Piston flange 44 can engage a capture mechanism on the rear of the syringe plunger (as, for example, described in U.S. Pat. No. 5,383,858).

Once mounting flanges 22a and 22b are inserted into receiving slots 66a and 66b, respectively, and piston 40 is in position to be received by the plunger, the operator rotates syringe 20 approximately 90 degrees such that mounting flanges 22a and 22b move behind and are engaged by receiving flanges 68a and 68b, respectively. Injector 10 may include a stop mechanism (not shown), for example, extending from at least one of the retaining slots 68a and 68b, to prevent rotation of syringe 20 more than 90 degrees. A flange 28 on the rear of the syringe 20 forward of flanges 22a and 22b substantially prevents injection fluid from the exterior of syringe 20 from entering injector 10. Flange 28 also assists in ensuring secure connection of syringe 20 to injector 10 and in positioning syringe 20 on injector 10 in a predetermined axial position relative to injector 10. Tactile, visual or audible feedback can be provided to the operator via, for example, cooperating members on syringe 20 (for example, on sealing flange 28) and injector 10 to inform the operator that a secure connection has been achieved. After securely attaching syringe 20 to injector 10, advancing piston 40 in a forward direction will apply a motive force to plunger 25 to advance the plunger forward within syringe 20, thereby forcing the contents of syringe 20 out of syringe tip 26 into the fluid path to the patient. Retracting piston 40 in a rearward direction will cause the plunger to move rearward within syringe 20, thereby drawing fluid into syringe 20.

Figure 2A:
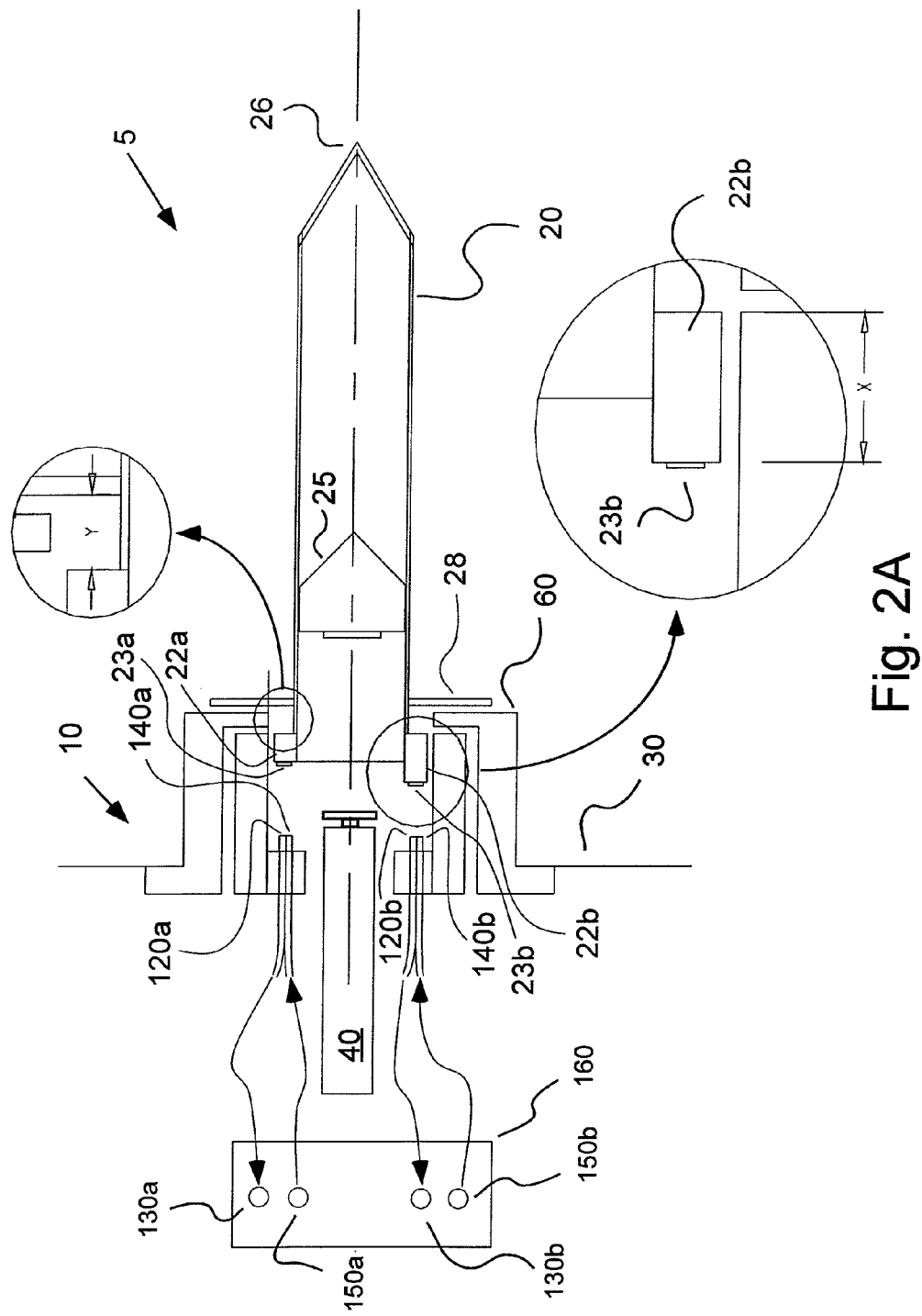
FIG. 2A illustrates a side, cross-sectional view of the injector system of FIG. 1.

In one embodiment of the present invention, the syringe is provided with at least one indicator element and the injector is provided with corresponding receiver(s)/sensor(s) to provide information on syringe configuration. A signal received by each receiver/sensor varies depending upon the position of the indicator element(s) upon the syringe or the distance between the indicator element(s) and the detection/reception point(s) on the injector. In the embodiment of FIGS. 1 and 2A, the indicator elements on syringe 20 are the rear surfaces of flanges 22a and 22b.

As illustrated, for example, in FIGS. 1 and 2A, syringe 20 can be positioned relative to injector 10 and receiver 120a and 120b in a known manner or position by abutment of the rear surface of flange 28 with the forward surface of injector face 60. A constant distance Y can be provided between the rear surface of flange 28 and the forward surfaces of flanges 22a and 22b, for example, to provide for proper and secure seating of flanges 22a and 22b behind retaining flanges 68a and 68b (see FIG. 1, not shown in FIG. 2A) of injector 10 when syringe 20 is securely connected to injector 10. By varying the axial thickness (represented by X for flange 22b) of one or both of flanges 22a and 22b, one can define various unique states that correspond to unique syringe configurations. As illustrated in FIG. 2A, the rear surface of flange 22b extends beyond the rear surface of the syringe barrel by a predetermined or known amount, while the rear surface of flange 22a is generally flush with the rear surface of the syringe barrel.

In general, the syringes of the present invention can be attached to an injector in any manner suitable to position one or more indicators thereof (for example, the rear surfaces of flanges 22a and 22b) in a manner that will result in a correct reading of syringe configuration. In the embodiment of FIG. 2A, flange 28 serves, in part, to reference the position of syringe 20 to injector 10 and prevents syringe 20 from traveling too far rearward during connection to injector 10. As clear to one skilled in the art, there are many alternative manners of attaching a syringe to an injector to properly position one or more indicators thereon.

As shown in FIGS. 1 and 2A, the flange 28 extends around the circumference of the syringe 20. However, the present invention contemplates that the flange 28 may be segmented or otherwise formed by one or more flanges, tabs or shoulder members positioned on and extending radially from the syringe 20.

Figure 2B:
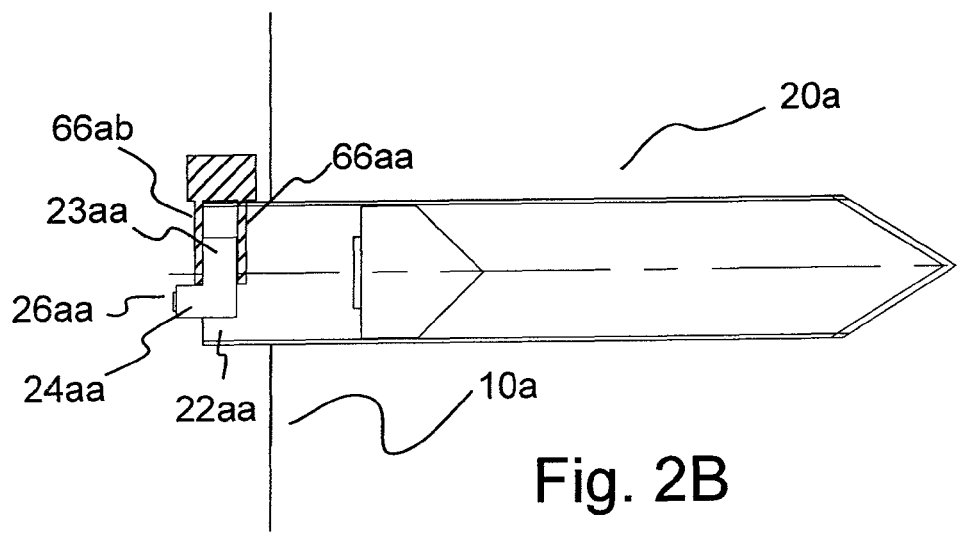
FIG. 2B illustrates a side, cross-sectional view of another embodiment of a syringe of the present invention attached to an injector.

FIG. 2B illustrates a syringe 20a including two, generally opposed attachment flanges 22aa and 22ab (not shown in FIG. 2B) that cooperate with spaced flanges or surfaces such as flanges 66aa and 66ab on an injector 10a to position syringe 20a at a predetermined axial position with respect to injector 10a. Flange 22aa includes a connecting section 23aa that seats between spaced flanges 66aa and 66ab and a rearward extending section 24aa. The axial position of the rearward surface 26aa of section 24aa can be varied between different types of syringes to provide information on syringe configuration as described above. Flange 22ab (not shown) can provide information on syringe configuration in a similar manner.

Figure 2C:
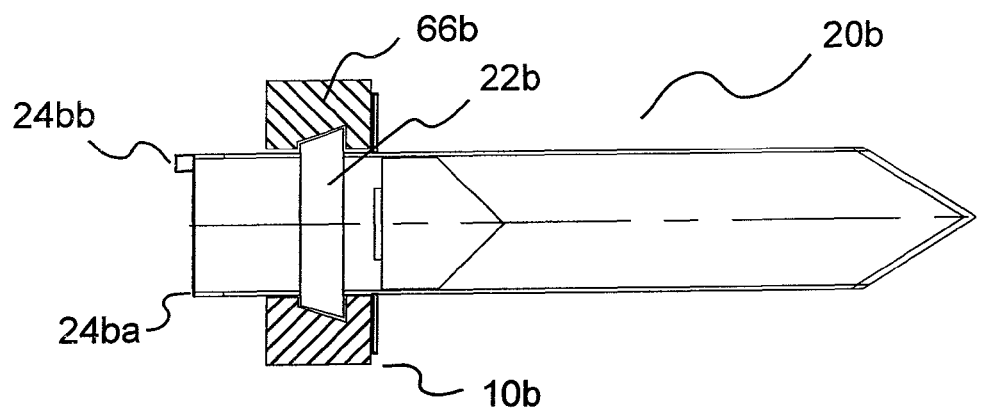
FIG. 2C illustrates a side, cross-sectional view of another embodiment of a syringe of the present invention attached to an injector.

As also clear to one skilled in the art, the indicators of the syringes of the present invention need not be part of or connected to an attachment flange or other attachment mechanism. For example, FIG. 2C illustrates a syringe 20b including a circumferential attachment flange 22b that cooperates with an attachment mechanism 66b of an injector 10b in a manner to removably attach syringe 20b to injector 10b. This system is described in PCT Publication No. WO 01/37903, the disclosure of which is incorporated herein by reference. In this embodiment, the axial position of the rear surface 24ba of the syringe wall (which can be varied among syringe types) can provide information on syringe configuration as described above. Additional or alternatively, on or more uniquely positioned indicators such as flange or projection 24bb can be provided on a rear portion of syringe 20b to provide information on syringe configuration as described above.

Figure 2D:
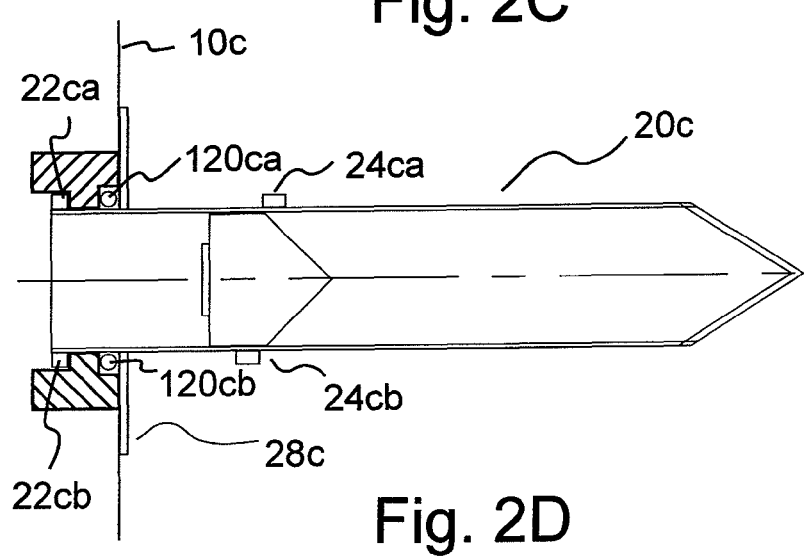
FIG. 2D illustrates a side, cross-sectional view of a further embodiment of a syringe of the present invention attached to an injector, in which the syringe includes indicators on the syringe barrel.

FIG. 2D illustrates a syringe 20c attached to, for example, injector 10c via flanges 22ca and 22cb in a manner described above for syringe 20. In the embodiment of FIG. 2D, indicators 24ca and 24cb are positioned on the syringe barrel rather than on a rear section of syringe 20c. Indicators 24ca and 24cb can, for example, transmit energy to receivers 120*ca* and 120*cb* through a transmissive flange 28*c* on syringe 20*c*.

Returning now to the embodiment of FIGS. 1 and 2A, receivers 120*a* and 120*b* can, for example, be fiber optic cables suitable to receive light signals transmitted from the rear surfaces of flanges 22*a* and/or 22*b*. Receiving fiber optic cables 120*a* and 120*b* carry the received light to sensors such as photodiodes 130*a* and 130*b*. The axial position of reception points of fiber optic cables 120*a* and 120*b* are preferably known and fixed relative to flange 28. In one embodiment, photodiodes available from Optek of Carrolton, Tex., under product number OPF422 were used.

In the embodiment of FIGS. 1 and 2A, reflective surface 23*a* and 23*b* (for example, a mirrored surface in the case that light energy is used) are provided on the rear surfaces of flanges 22*a* and 22*b* to transmit/redirect light from the rear surfaces of flanges 22*a* and 22*b* to receiving fiber optic cables 120*a* and 120*b*. In one embodiment, protected aluminum mirrors available from Edmund Industrial Optics of Barrington, N.J., under product stock number J32-354 were used. Light is directed toward mirrors 23*a* and 23*b* such that light will be transmitted to receiving fiber optic cables 120*a* and 120*b*. In the embodiment of FIGS. 1 and 2, split fiber optic cabling was used. Transmitting fiber optic cables 140*a* and 140*b* were arranged adjacent receiving fiber optic cables 120*a* and 120*b* to transmit light from light sources 150*a* and 150*b* (for example, laser diodes available from Sanyo Semiconductor Corporation of Allendale, N.J., under product number DL-3144-0) to mirrors 23*a* and 23*b*. Suitable fiber optic cabling is available, for example, from Omron of Santa Clara, Calif., under product number E32-DC200.

Figure 3:
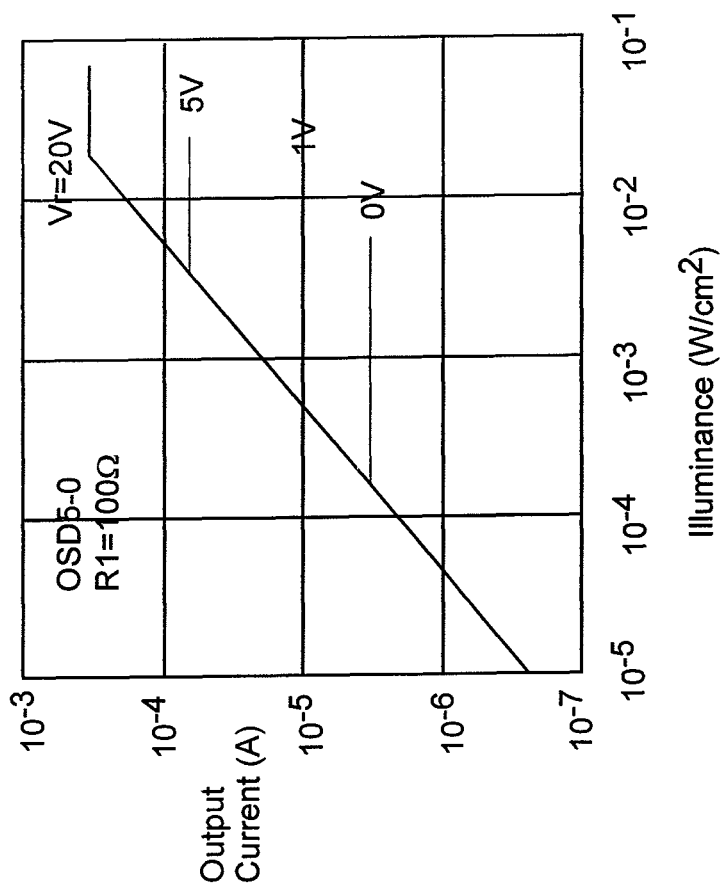
FIG. 3 illustrates the output signal of a photodiode as a function of illuminance.

In general, the electric signal produced by a photodiode is proportional to the illuminance (for example, in watts/cm$^2$) of the radiant energy incident upon the photodiode. Indeed, the output signal of a photodiode is generally linear with respect to the illuminance applied to the photodiode junction as illustrated in FIG. 3.

Figure 4:
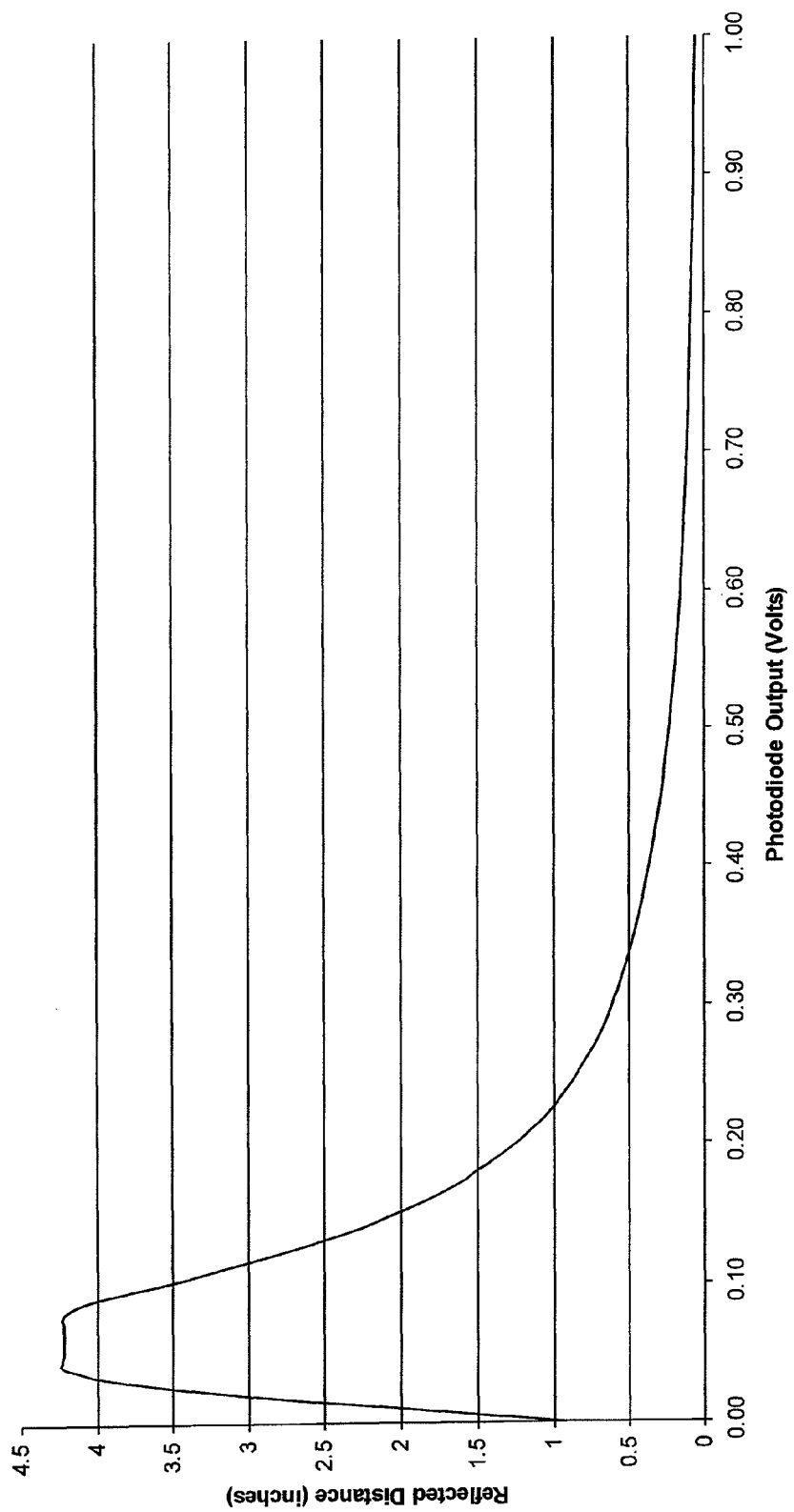
FIG. 4 illustrates the output signal of a photodiode as a function of distance.

The illuminance of the incident radiant energy and thus the amplitude of the electric signal (for example, measured current and/or voltage) produced by a photodiode is indirectly proportional to the linear distance between the light source (mirrors 23*a* and 23*b* in FIG. 2A) and the point of reception (fiber optic receivers 120*a* and 120*b*). Circuitry and/or software as known in the art can be used to translate the measured signal into a syringe configuration (using, for example, one or more comparison or lookup tables). The output signal of an Optek OPF422 photodiode used in one embodiment of the present invention is illustrated as a function of distance in FIG. 4.

As clear to one skilled in the art, sensors such as photodiodes 130*a* and 130*b* can be placed in direct communication with the light source (mirrors 23*a* and 23*b* in FIG. 2A) without intervening fiber optic cabling. However, use of fiber optic cabling can facilitate retrofitting of existing injectors with the encoding system of the present invention. Moreover (and as further discussed in connection with FIG. 5 below) use of fiber optic cabling and/or other transmitting media and the associated remote positioning of sensors and/or energy sources assists in preventing interference from extraneous energy sources (for example, ambient light) and in removing sensors from areas in which spilled or leaked injection media (for example, imaging contrast media) can have an adverse effect upon the sensors and/or energy sources. Moreover, fiber optic cabling can assist in positioning sensor/light source electronics away from the magnetic field (for example, within a shielded housing 160) of MRI equipment to reduce interference with the MRI imaging equipment. Fiber optic cabling is a particularly efficient means of transmitting light. Indeed, measurements have shown that the reflection coefficient from a dielectric interface within, for example, a high quality optical fiber exceeds 0.9999. See, for example, *Handbook of Optics*, McGraw-Hill, p. 13-6. Furthermore, as also clear to one skilled in the art, a light or other energy source (for example, a laser or an LED) can be positioned on the rear surface of flanges 22*a* and 22*b* rather than using reflected energy.

The number of states or configurations detectable by the encoding systems of FIG. 2A depends, for example, upon the resolution of sensors such as photodiodes 130*a* and 130*b*. In general, photodiodes are relatively sensitive to even small changes in the distance between the transmittance point of the light and the reception point of the light, enabling the definition of a relatively large number of discreet states or configurations over a relatively short distance.

The number of states or configurations detectable also depends upon the number of indicator/sensor parings. For example, if seven discreet states are detectable using a single indicator/sensor pairing, 49 states are detectable using two such pairings. Table 1 provides one embodiment of a state table for one Optek OPF422 photodiode used in the present invention. A disengage state and six additional states, corresponding to different lengths X as described above, are defined by associating or correlating discreet ranges of voltage output with those states.

TABLE 1

| Distance (inches) | Min (V) | nom (V) | max (V) |
| --- | --- | --- | --- |
| Disengage | 0.1 | 0.105 | 0.11 |
| State 1 | 0.13 | 0.135 | 0.14 |
| State 2 | 0.16 | 0.165 | 0.17 |
| State 3 | 0.19 | 0.195 | 0.2 |
| State 4 | 0.225 | 0.23 | 0.235 |
| State 5 | 0.275 | 0.28 | 0.285 |
| State 6 | 0.395 | 0.4 | 0.405 |

In addition to providing additional detectable states or configuration, multiple indicators can be provided for calibration or to provide data integrity. Moreover, a single sensor can be used with multiple indicators. In certain situations, it can also be desirable to pulse the transmitted energy to improve detectability.

Figure 5:
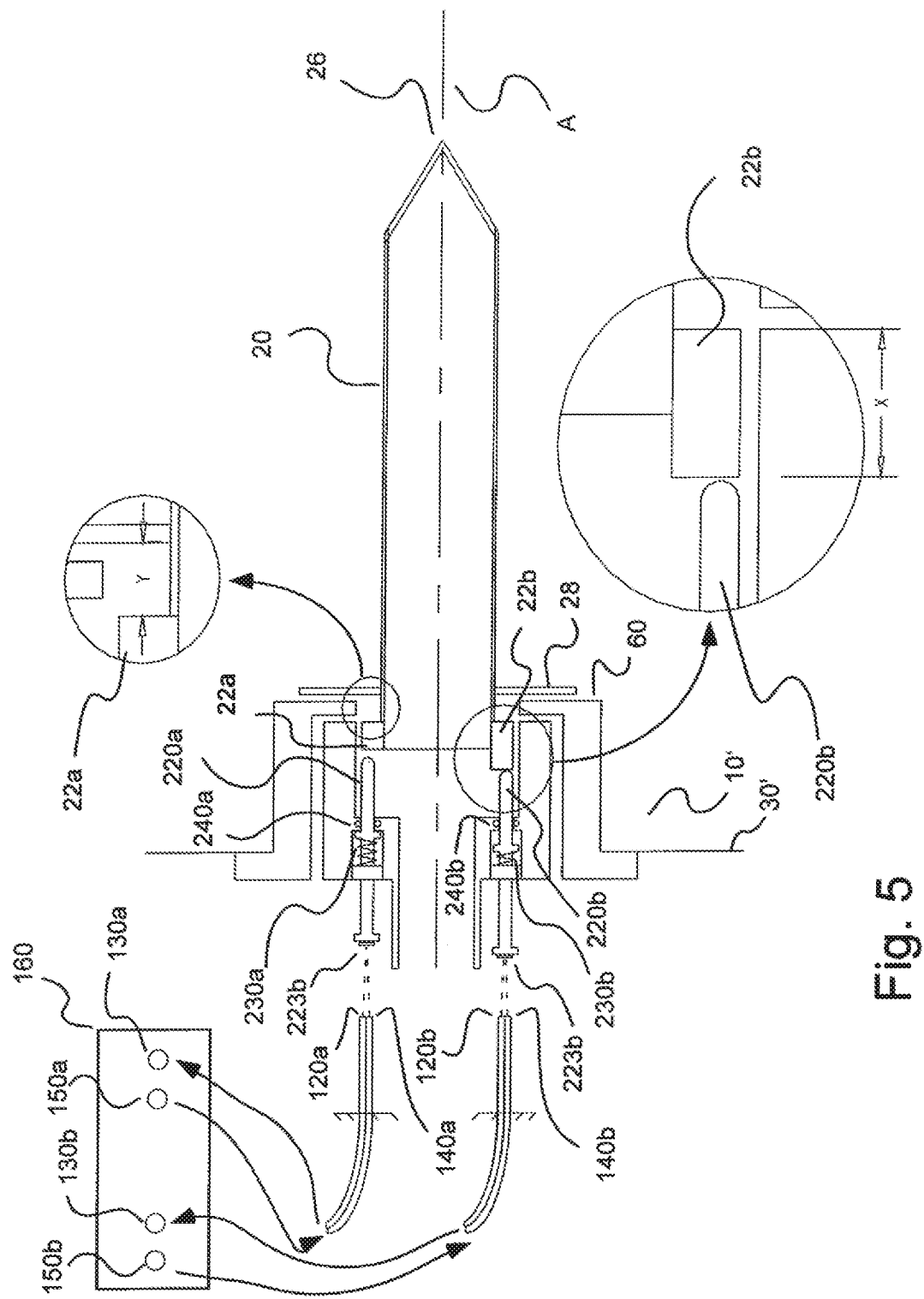
FIG. 5 illustrates a side, cross-sectional view of another embodiment of an injector system of the present invention.
Figure 6B:
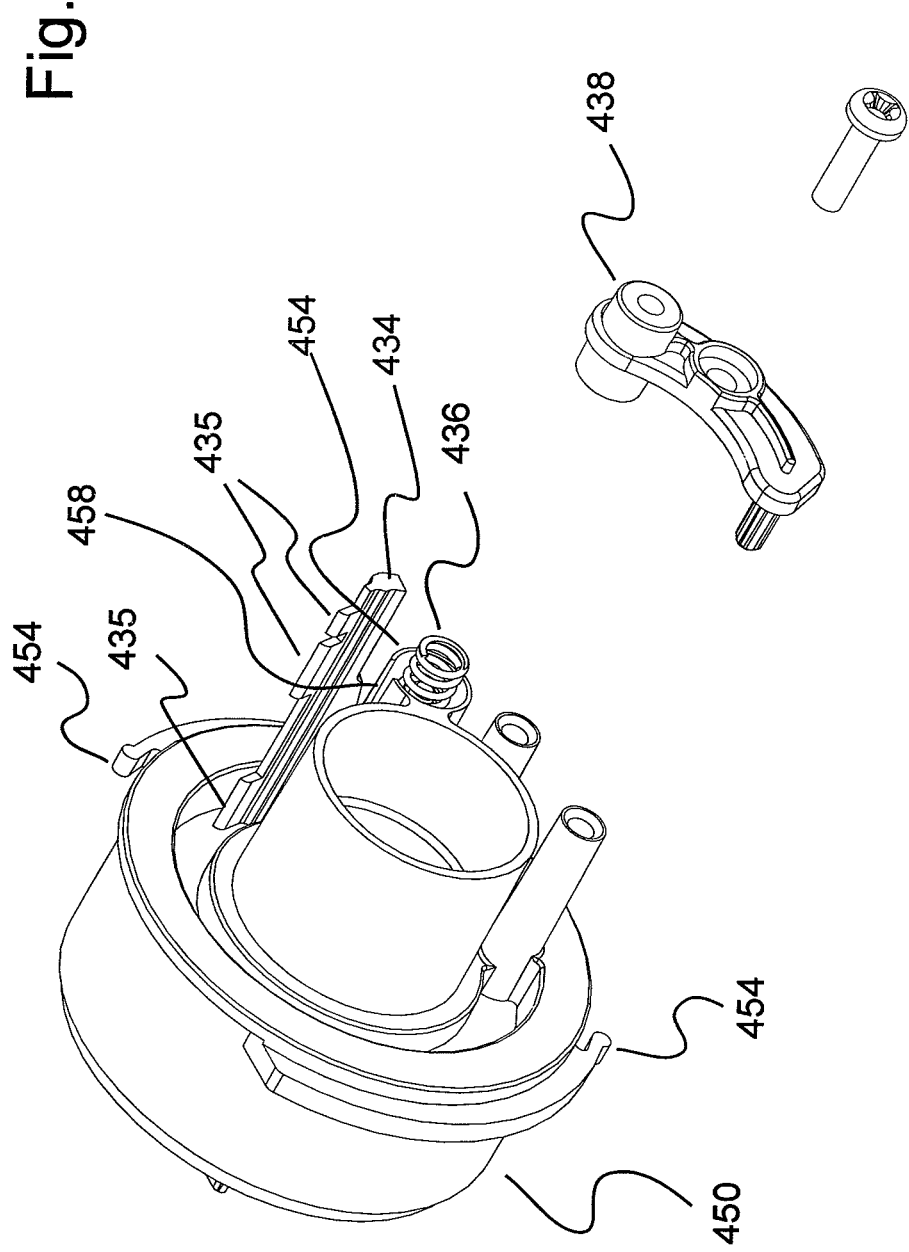
FIG. 6B illustrates a rear perspective view of the syringe interface of FIG. 6A in a partially assembled state.
Figure 6D:
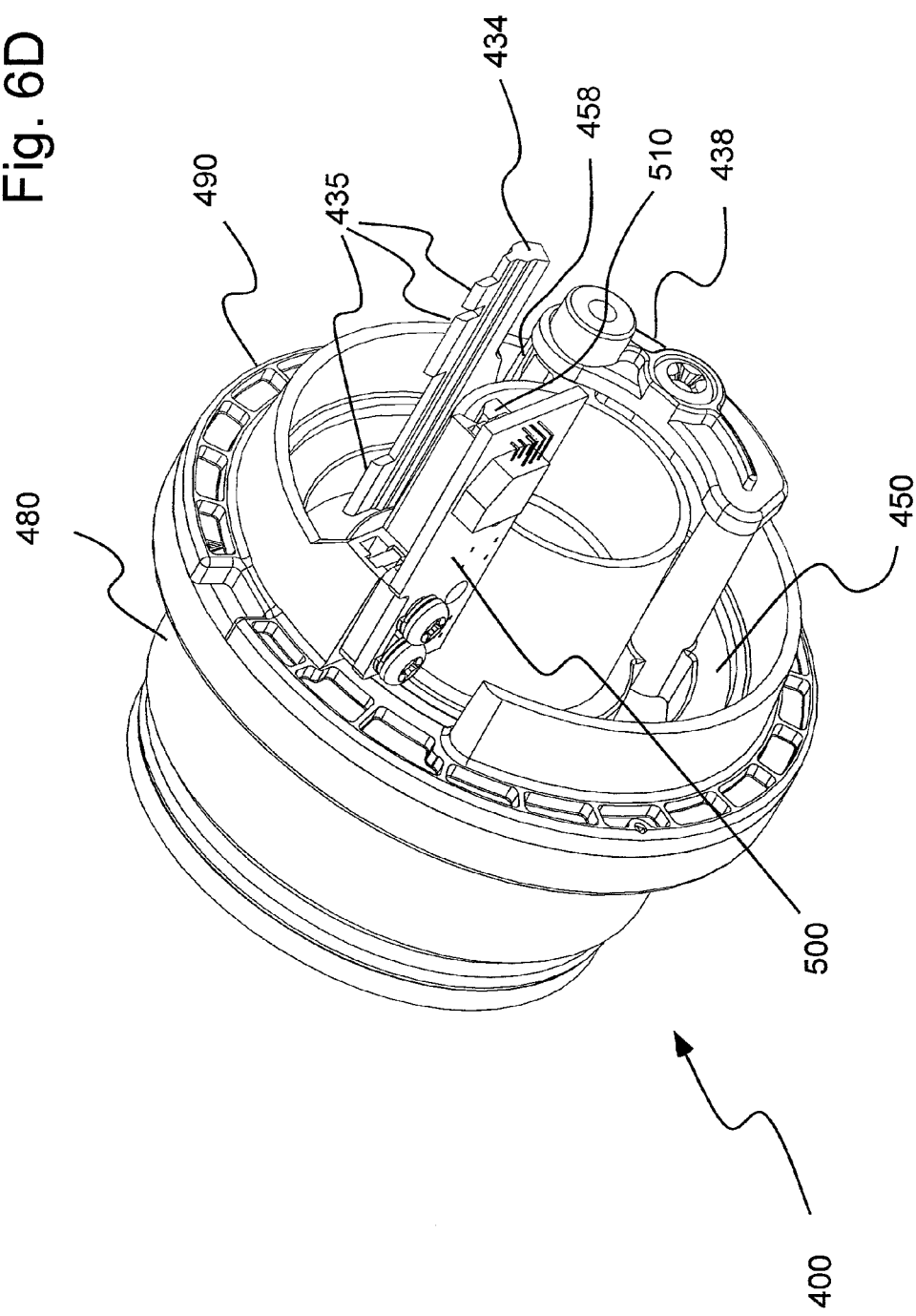
FIG. 6D illustrates a rear perspective view of the syringe interface of FIG. 6A in a fully assembled state.

In the embodiment of FIG. 5, injector 10' includes contact members such as push pins 220*a* and 220*b* that are slideably disposed within injector housing 30' such that they are contacted by the rear surfaces of at least one of flanges 22*a* and 22*b*, respectively. Push pins 220*a* and 220*b* are preferably biased in a forward position by, for example, springs 230*a* and 230*b*. In the embodiment of FIG. 5, the rear surfaces of push pins 220*a* and 220*b* include reflective surfaces such as mirrors 223*a* and 223*b* as described above. Mirrors 223*a* and 223*b* are suitably positioned to reflect light from light sources 150*a* and 150*b* exiting transmitting fiber optic cables 140*a* and 140*b* to receiving fiber optic cables 120*a* and 120*b* and therethrough to photodiodes 130*a* and 130*b*. The output signal of photodiodes 130*a* and 130*b* is proportional to the distance between the rear surface of push pins 220*a* and 220*b* and receiving fiber optic cables 120*a* and 120*b*, respectively, as described above. The distance between the rear surface of push pins 220*a* and 220*b* and receiving fiber optic cables 120*a* and 120*b* is directly proportional to the axial position of the rear surfaces of flanges 22*a* and 22*b*, respectively.

Sealing members such as O-rings 240*a* and 240*b* can be provided to further assist in preventing spilled or leaked injection fluid from coming into contact with the optics (or other transmission and/or sensing media) used in the injectors of the present invention.

Although the indicators in the embodiment of FIGS. 1, 2A and 5 of the present invention have been shown to be positioned on flanges 22a and 22b within housing 30 or housing 30' of injector 10 or injector 10', respectively, when syringe 20 is attached to injector 10 or injector 10', the indicators can be positioned anywhere on syringe 20 (compare, for example, FIGS. 2A through 2D). Moreover, energy sources other than light sources can be used in the present invention. Any energy source/sensor or receiver pairing in which the output of the sensor is proportional to the distance the energy is transmitted from the indicator is suitable for use in the present invention. For example, any waveform type energy (for example, sonic energy or electromagnetic energy) can be used.

In case fiber optic cable is used in the above embodiments to transmit light from an energy source to a sensor or receiver, preferably dynamic change or deformation (for example, bending or twisting) of the fiber optic cable is minimized. Because of the manner in which light propagates through fiber optic cable (that is, reflecting or bouncing between the sides of the cable as it passes therethrough), twisting and/or bending of the fiber optic cable changes the path of the fiber optic cable, thereby changing the path of the light. Light beams thus may exit the cable at different angles than for which the system was calibrated and can cause a different amount of light to reach a receiver. If the changes are substantial, an erroneous signal can result.

FIGS. 6A through 8B illustrate another embodiment of the present invention in which a syringe (or, for example, a syringe adapter as known in the art) contacts and displaces a push pin or push pins to provide syringe configuration or information to an injector.

As illustrated, for example, in FIGS. 6A-6D, a syringe interface or mount 400 (shown assembled, for example, in FIG. 6D) includes a push pin 432 that is preferably part of or formed with a shutter mechanism 430. Alternately, the push pin 432 may be a separate part that is connected or attached to the shutter mechanism 430. A rubber boot or seal 420 may be placed over the push pin 432 to prevent contrast fluid or other material from entering the syringe interface 400 or bushing seat 450.

When assembled, the push pin 432 (and the shutter mechanism 430) protrudes in a forward axial direction from a rear surface of a rotatable bushing seat 450. In the embodiment of FIGS. 6A-8B, bushing seat 450 is rotatable within an interface housing 480 (see, for example, FIG. 6C). Interface housing 480 includes slots 482a and 482b through which, for example, flanges 822a and 822b (not shown) of syringe adapter 800, to which syringe 700 is attached (illustrated, for example, in FIGS. 7D and 7F), can pass to be seated in slots 452a and 452b (see, for example, FIG. 7C) of bushing seat 450. After seating syringe adapter 800, syringe 700 and adapter 800 are rotated approximately ¼ turn or 90° (thereby rotating bushing seat 450) relative to interface housing 480 so that flanges 822a and 822b of syringe adapter 800 are rotated behind and into cooperation with retention flanges 484a and 484b of interface housing 480 to removably attach syringe adapter 800/syringe 700 to syringe mount 400 as described above. Flange 828 assists in forming a secure connection of syringe adapter 800 to interface 400 and in ensuring the proper axial position of syringe adapter 800 relative to interface 400 as discussed above. Rotation of bushing seat 450 relative to housing 480 as a result of the connecting motion of syringe adapter 800 also rotates a shutter 434 of a shutter mechanism 430 into operative connection with a sensor circuit board 500 (see, for example, FIG. 7E) as described below.

In general, a syringe such as a syringe 700 that is not suitable for direct attachment to syringe interface 400 or that does not have one or more attachment flanges that are adapted/dimensioned to provide information on syringe configuration can be attached to syringe interface 400 through use of intermediate adapter 800 as described above. Flange 822a, for example, is dimensioned to provide information on the syringe configuration of syringe 700. Adapter 800 can, for example, include a syringe attachment mechanism 860 to attach syringe 700 thereto via flanges 722a and 722b (not shown) of syringe 700 in a manner described above. As known in the art, adapters have many types of syringe attachment mechanisms that can be used to adapt a wide variety of syringes for attachment to syringe interface 400. Examples of syringe adapters suitable for use in the present invention are disclosed, for example, in PCT Publication No. WO 01/08727, the contents of which are incorporated herein by reference.

Syringe mount 400 can provide tactile, visual or audible feedback to the operator and to injector 10 to inform the operator that a secure connection has been achieved. For example, bushing seat 450 can include flexing extensions 454 that cooperates with a receptacle 486 on interface housing 480 to provide tactile and audible feedback. In that regard, rotation of flexing extensions 454 into and out of receptacles 486 requires radial inward flexing of flexing extensions 454. The cooperation of extensions 454 and receptacles 486 can also provide resistance to rotation of, for example, syringe adapter 800 or syringe 20 and bushing seat 450 in a counterclockwise direction to release syringe adapter 800 or syringe 20 from cooperation with retention flanges 484a and 484b (that is, toward the position of the left side of FIGS. 7A through 7C).

As discussed above, push pin 432 is moved rearward upon contact with syringe adapter 800 a distance determined by the axial thickness of at least one of syringe adapter flanges 822a or 822b. Push pin 432 is in operative connection with shutter assembly 430 such that axial motion of push pin 432 is translated to axial motion of shutter assembly 430. In the embodiment to FIGS. 6A through 8B, as discussed above, push pin 432 preferably includes a cap or sealing member 420 seated thereon. The assembly of push pin 432 and shutter assembly 430 are seated in a rearward extending well 454 formed on the rear of bushing seat 450. Shutter 434 of shutter assembly 430 moves axially through slot 458 of well 456. Push pin 432 and shutter assembly 430 are preferably biased in a forward or reference position (corresponding, for example, to a state in which no syringe is connected to syringe interface 400) by, for example, a spring 436. Spring 436 is biased against a shutter plate 438 that operates to secure push pin 432 and shutter assembly 430 within well 454.

Figure 7A:
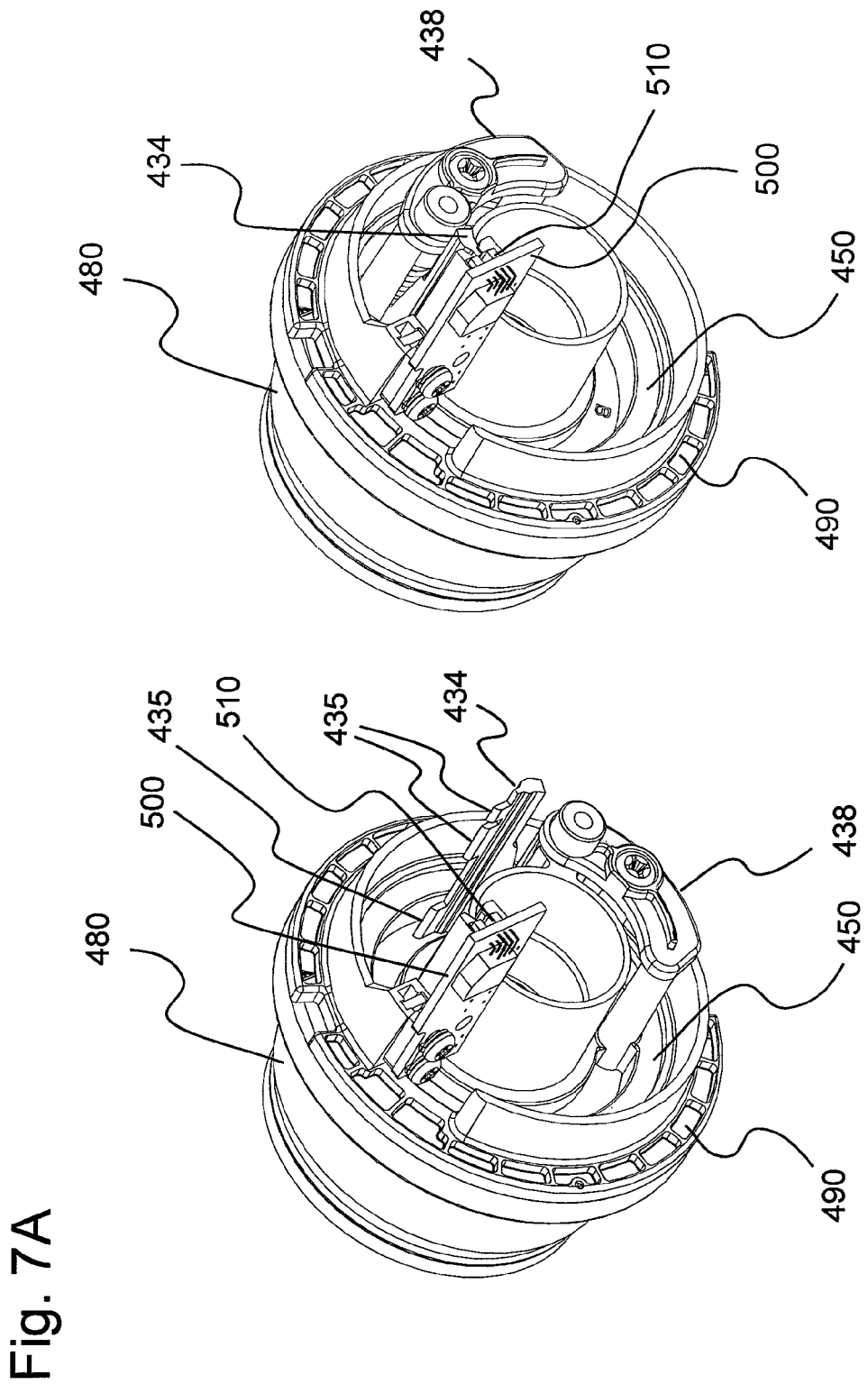
FIG. 7A illustrates a rear perspective view of the syringe interface of FIG. 6A wherein the seating bushing is illustrated in a disengaged position (left) and rotated to an engaged position (right).
Figure 7B:
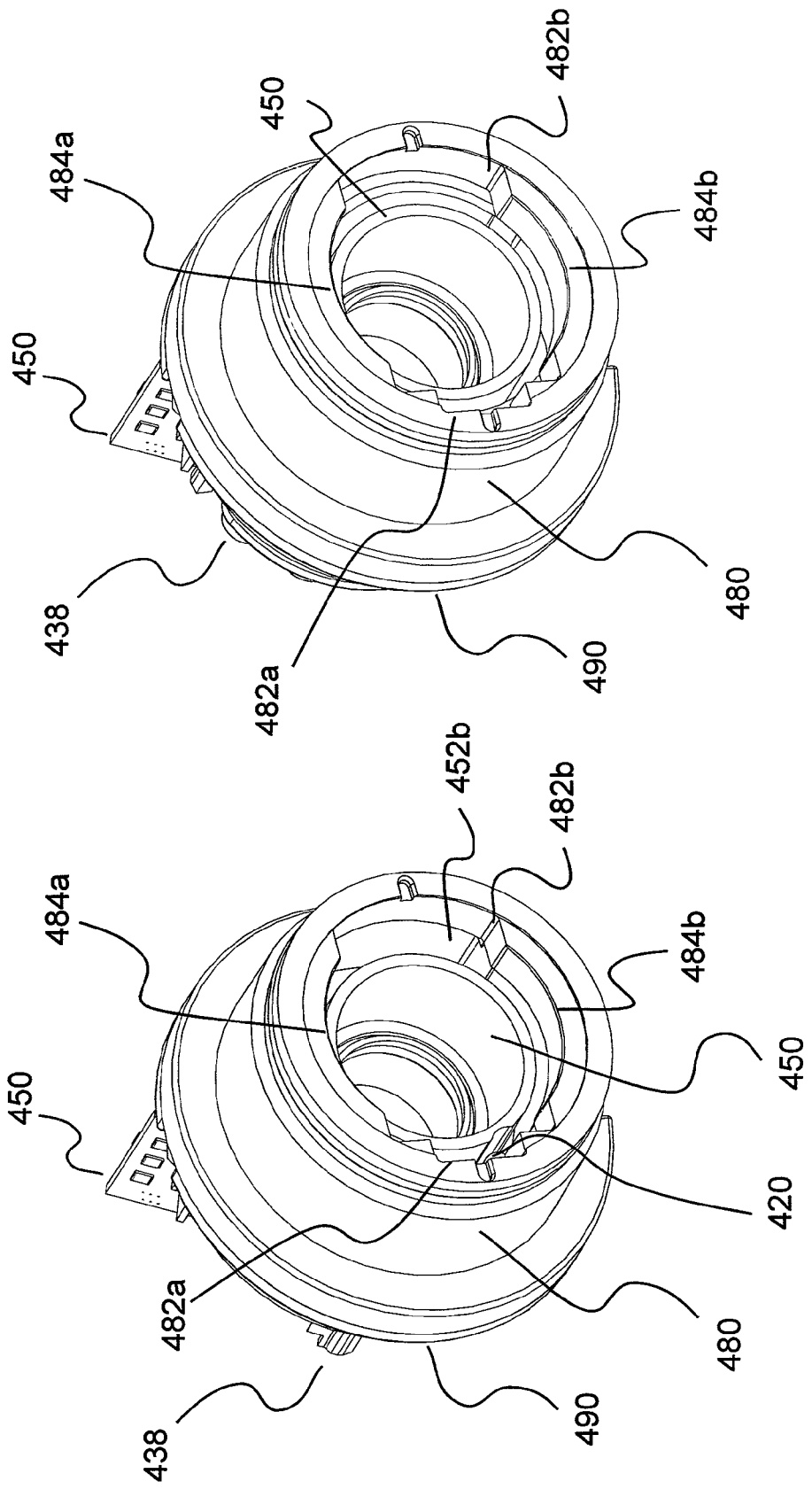
FIG. 7B illustrates a front perspective view of the syringe interface of FIG. 6A wherein the seating bushing is illustrated in a disengaged position (left) and rotated to an engaged position (right).
Figure 7C:
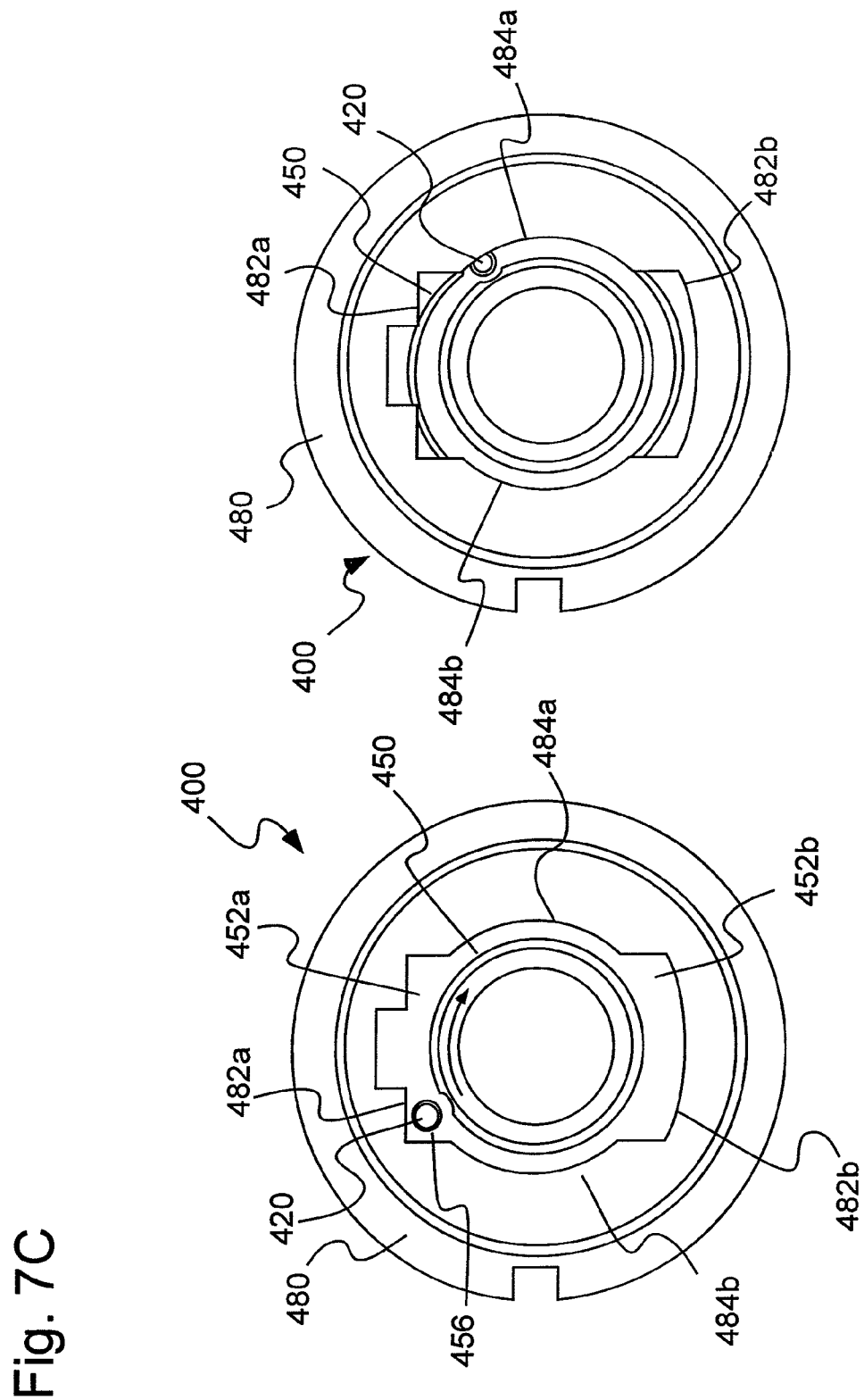
FIG. 7C illustrates a front view of the syringe interface of FIG. 6A wherein the seating bushing is illustrated in a disengaged position (left) and rotated to an engaged position (right).
Figure 7D:
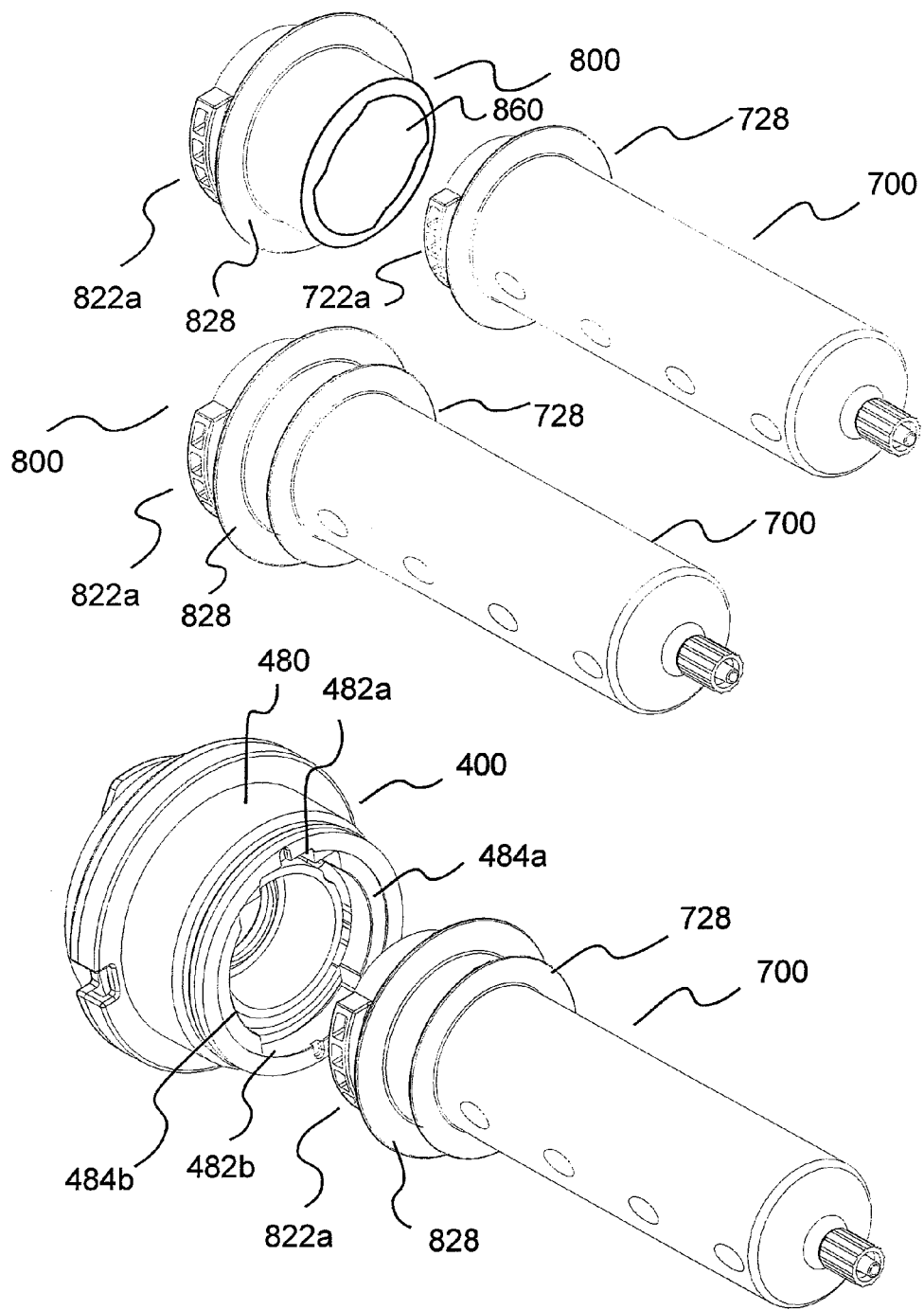
FIG. 7D illustrates a front perspective view of the syringe interface of FIG. 6A with a syringe aligned for engagement therewith and a front perspective view of an adapter for use with the syringe interface.
Figure 7E:
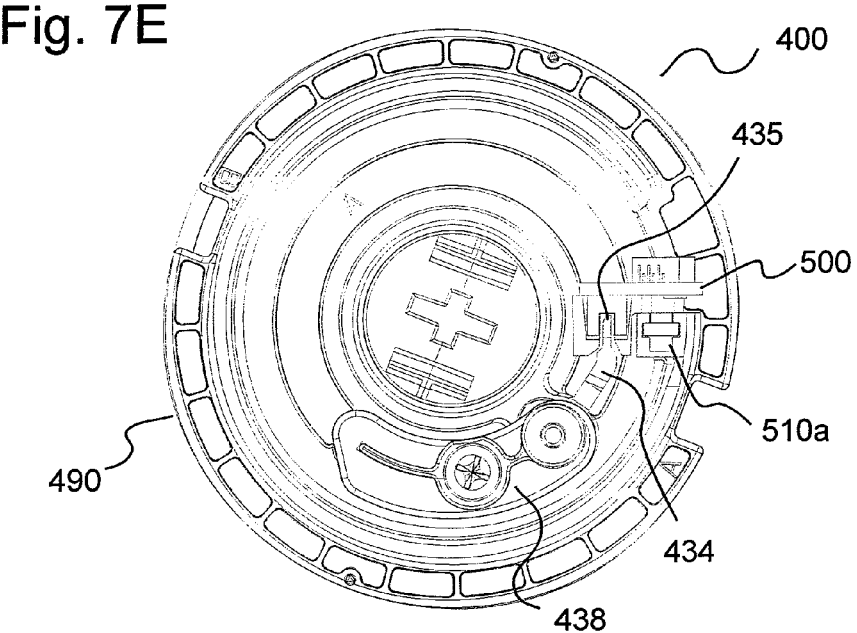
FIG. 7E illustrates a rear view of the syringe interface of FIG. 6A with a syringe connected thereto.
Figure 7F:
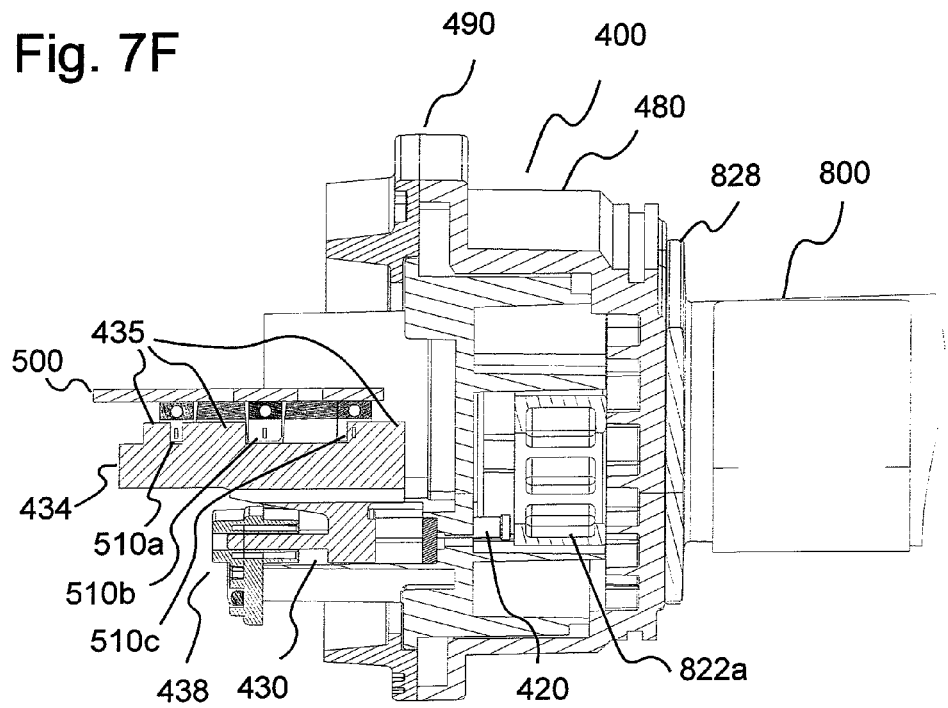
FIG. 7F illustrates a side, cross-sectional view of the syringe interface of FIG. 6A with a syringe connected thereto.

As discussed above, shutter 434 is linearly translated a distance determined by the flange length of the engaged syringe/adapter (see, for example, FIG. 7F, showing syringe adapter 800 of type 4 from Table 2 below attached to syringe interface 400). The movement of shutter 434 causes blocking extensions 435 of shutter 434 to block or unblock a light source/receiver pair in each of a plurality of sensors 510a, 510b and 510c positioned on circuit board 500. The digital output of sensors 510a-c provides the configuration of the syringe or adapter that is engaged on the injector.

Syringe interface 400 provides the ability to accurately detect (1) whether a syringe/adapter is engaged thereto as well as (2) multiple different syringes having different flange sizes as described above. In the embodiment of FIGS. 6A through 8B, three sensors 510a-c are preferably used to provide a maximum of eight combinations ($2^3=8$) of sensor on/off states to associate with syringe or adapter configurations. As described above, shutter 434 is rotated into communication with sensors 510a-c upon engagement of a syringe or adapter. Thus, a disengaged state corresponds to the state when all three sensors are on. All of sensors 510a-c are preferably placed on the same side of shutter 434 to provide for such rotation. Preferably, the state corresponding to all sensors being off is not used to determine a syringe state because of difficulties in testability. In that regard, it would be difficult to determine if sensors 510a-c were blocked or malfunctioning in that state. Blocking extensions 435 and the openings therebetween are preferably sufficiently wide to ensure total activation or deactivation of sensors 510 a-c.

Table 2 provides a representative list of syringe/adapters, corresponding flange lengths and sensor states for one embodiment of the present invention.

TABLE 2

Sensor State List

| Syringe/<br>Adapter<br>Type | Flange<br>Length<br>(in.) | Displacement<br>(in.) | Sensor<br>510a State | Sensor<br>510b State | Sensor<br>510c State |
|---|---|---|---|---|---|
| 1 | 0.25  | 0.032 | Off | On  | Off |
| 2 | 0.318 | 0.096 | Off | Off | On  |
| 3 | 0.386 | 0.162 | On  | Off | On  |
| 4 | 0.455 | 0.229 | On  | On  | Off |
| 5 | 0.515 | 0.288 | Off | On  | On  |

FIG. 8A illustrates the dimensions of one embodiment of shutter 434 and the states for each of the sensors/adapters of Table 2 for a given sensor spacing.

The shutter mechanism 430 and sensors 510, in a preferred embodiment, reliably read multiple syringe and/or adapters of similar geometry within a given range of desired operation. A tolerance analysis was performed on the sensing mechanism to minimize or substantially prevent misreads. Misreads can occur, for example, if the entire "sweet spot" of a sensor is not blocked or unblocked with respect to a specific syringe state. In several embodiments of the present invention, Omron EE-SX1103 photomicrosensors available from Omron Electronics, Inc. of Schaumburg, Ill., were used as sensors 510a-c. Further information on these sensors is provided in the Omron Electronics, Inc. specification sheet for the EE-SX1103 photomicrosensor, the disclosure of which is incorporated herein by reference. For those sensors, the distance between the fully open and fully closed state is 0.020 in. Circuit board 500 (upon which sensors 510a-c are mounted) is adjustable in position in the direction of the movement axis of push pin 432 to facilitate alignment.

Preferably, a mechanical calibration is performed upon installation of sensor circuit board 500. In the embodiment of FIGS. 8A and 8B, for example, a calibration was performed using a slug corresponding to syringe/adapter type 1 (see Table 2) engaged on syringe interface 400 (see FIG. 7D). During the calibration, the top surface of top-most sensor 510a is aligned with the top of shutter 434 as illustrated by the arrow in FIG. 8A. This position biases the push pin/shutter assembly slightly and removed tolerances from the system. (Several remaining tolerances correspond to the flange thickness on the syringes or adapters, the sensor placement and the notch/blocking extension dimensions of shutter 434 (see FIGS. 8A and 8B)). These tolerances can contribute to the "sweet spot" of the sensor(s) moving relative to the notches/blocking extensions on shutter 434.

FIG. 8B illustrates representative misread plays (that is, the distance between a sensor sweet spot and the edge of an adjacent blocking extension 435) for a machined steel shutter assembly having the dimensions set forth in FIG. 8A. In FIG. 8B, the shutter displacement corresponds to a syringe/adapter of type 3 engaged within syringe interface 400. Distinct states are readily obtained and associated tolerances indicate that misreads should not occur. FIG. 8C illustrates test results obtained. The hatched regions between states in FIG. 8C represent transition zones in which sensors 510a-c were in the process of changing states.

The foregoing description and accompanying drawings set forth the preferred embodiments of the invention at the present time. Various modifications, additions and alternative designs will, of course, become apparent to those skilled in the art in light of the foregoing teachings without departing from the scope of the disclosed invention. The scope of the invention is indicated by the following claims rather than by the foregoing description. All changes and variations that come within the meaning and range of equivalency of the claims are to be embraced within their scope.

What is claimed is:

1. An injector system comprising:

a powered injector comprising a drive member, an energy source, at least one sensor in communication with the energy source for detecting energy from the energy source, and at least one contact member axially movable in a direction of the drive member, the at least one contact member in communication with the at least one sensor; and a syringe comprising at least a first indicator indicative of a syringe configuration positioned on the syringe at a predetermined position, wherein the syringe configuration is detectable by the at least one sensor based on the predetermined position of the at least a first indicator when the syringe is attached to the powered injector, wherein the at least one contact member contacts the at least a first indicator to move the at least one contact member when the syringe is attached to the powered injector such that a signal from the energy source detected by the at least one sensor is proportional to a distance moved by the at least one contact member to indicate the syringe configuration, and wherein a rear surface of the first indicator transmits energy to the at least one sensor and comprises a surface that transmits energy to the at least one sensor by reflecting energy from the energy source to the at least one sensor.

2. The injector system of claim 1, comprising a surface in operative connection with the at least one contact member transmitting energy to the sensor;

wherein the surface is a rear surface of the at least one contact member, wherein the rear surface of the at least one contact member comprises a reflective surface to reflect energy from the energy source to the at least one sensor, wherein the energy is light energy; and wherein the reflective surface of the contact member is a mirrored surface.

3. The injector system of claim 2, wherein the at least a first indicator is a rear surface of an attachment flange on a rear portion of the syringe.

4. An injector system comprising:
- at least one syringe comprising at least a first indicator positioned on the at least one syringe at a predetermined position, the predetermined position of the at least a first indicator being associated with information about a syringe configuration; and
- a powered injector comprising a drive member, an energy source, at least one sensor for detecting energy from the energy source, and at least a first contact member axially movably disposed in the powered injector, the at least a first contact member positioned to contact the at least a first indicator when the at least one syringe is attached to the powered injector such that an axial position of the at least a first contact member is determined by a position of the at least a first indicator, wherein a change in the axial position of the at least a first contact member as a result of contact with the at least a first indicator indicates the syringe configuration, and wherein an amount of energy from the energy source detected by the at least one sensor is proportional to an axial distance moved by the at least a first contact member to indicate the syringe configuration;
- wherein the powered injector further comprises a plurality of sensors and at least a first shutter mechanism in operative connection with the at least a first contact member, each of the plurality of sensors having an on state and an off state, the at least a first shutter mechanism comprising at least one cooperating member to cooperate with at least one of the plurality of sensors to place the sensor in the on state or the off state, wherein each of the on state and the off state of the plurality of sensors provides a digital code corresponding to information on the syringe configuration.

5. The injector system of claim 4, wherein the at least a first indicator is positioned on a rear surface of an attachment flange of the syringe.

6. The injector system of claim 4, wherein the at least a first shutter mechanism comprises a plurality of cooperating members.

7. The injector system of claim 6, wherein the plurality of sensors are optical sensors and the plurality of cooperating members are spaced opaque members operable to block transmission of light to the plurality of sensors.

8. An injector for use with a syringe comprising at least a first indicator positioned thereon, the position of the at least a first indicator on the syringe being associated with a syringe configuration, the injector comprising:
- a drive member;
- an energy source;
- at least one sensor;
- at least a first contact member axially movably disposed in the injector, the at least a first contact member positioned to contact the at least a first indicator when the syringe is in operative connection with the injector such that an axial position of the at least a first contact member is determined by a position of the at least a first indicator, wherein a change in the axial position of the at least a first contact member as a result of contact with the at least a first indicator indicates the syringe configuration and wherein an amount of energy from the energy source detected by the at least one sensor is proportional to an axial distance moved by the at least a first contact member to indicate the syringe configuration;
- a plurality of sensors; and
- at least a first shutter mechanism in operative connection with the at least a first contact member, each of the plurality of sensors having an on state and an off state, the at least a first shutter mechanism comprising at least one cooperating member to cooperate with at least one of the plurality of sensors to place the sensor in the on state or the off state, wherein each of the on state and the off state of the plurality of sensors provides a digital code corresponding to information on the syringe configuration.

9. The injector of claim 8, wherein the at least a first shutter mechanism comprises a plurality of cooperating members.

10. The injector of claim 9, wherein the plurality of sensors are optical sensors and the at least one cooperating members are spaced opaque members operable to block transmission of light to the plurality of sensors.

11. The injector of claim 10, wherein the at least a first indicator is positioned on a rear surface of an attachment flange of the syringe and causes the at least a first contact member to move in an axial direction.

12. The injector of claim 11, wherein the at least a first contact member is slidably positioned on a bushing that is rotatable about an axis of the syringe.

13. The injector of claim 12, wherein the at least a first shutter mechanism is attached to the at least a first contact member and is rotated into cooperation with the plurality of sensors upon rotation of the bushing to attach the syringe to the injector.

14. The injector of claim 8, wherein the at least a first indicator is positioned on a rear surface of an attachment flange of the syringe.

* * * * *